(12) United States Patent
Yonekawa et al.

(10) Patent No.: US 10,439,143 B2
(45) Date of Patent: Oct. 8, 2019

(54) ADDITIVE FOR LIGHT-EMITTING LAYER IN LIGHT-EMITTING ELECTROCHEMICAL CELL, COMPOSITION FOR FORMING LIGHT-EMITTING LAYER IN LIGHT-EMITTING ELECTROCHEMICAL CELL, AND LIGHT-EMITTING ELECTROCHEMICAL CELL

(71) Applicant: Nippon Chemical Industrial Co., Ltd., Tokyo (JP)

(72) Inventors: Fumihiro Yonekawa, Tokyo (JP); Yohei Mizuguchi, Tokyo (JP)

(73) Assignee: NIPPON CHEMICAL INDUSTRIAL CO., LTD., Tokyo (JP)

( * ) Notice: Subject to any disclaimer, the term of this patent is extended or adjusted under 35 U.S.C. 154(b) by 0 days.

(21) Appl. No.: 15/739,837

(22) PCT Filed: Jul. 22, 2016

(86) PCT No.: PCT/JP2016/071490
§ 371 (c)(1),
(2) Date: Dec. 26, 2017

(87) PCT Pub. No.: WO2017/018328
PCT Pub. Date: Feb. 2, 2017

(65) Prior Publication Data
US 2018/0366646 A1 Dec. 20, 2018

(30) Foreign Application Priority Data

Jul. 27, 2015 (JP) ................................. 2015-148135
Jul. 20, 2016 (JP) ................................. 2016-142758

(51) Int. Cl.
*H01L 51/00* (2006.01)
*C07F 9/54* (2006.01)
(Continued)

(52) U.S. Cl.
CPC ............ *H01L 51/005* (2013.01); *C07C 69/78* (2013.01); *C07C 69/80* (2013.01); *C07C 69/96* (2013.01);
(Continued)

(58) Field of Classification Search
None
See application file for complete search history.

(56) References Cited

U.S. PATENT DOCUMENTS 5,679,482 A * 10/1997 Ehrenberg .......... H01M 2/1653
204/296
5,682,043 A 10/1997 Pei et al.
(Continued)

FOREIGN PATENT DOCUMENTS

EP 2790236 A1 10/2014
JP 10-506747 A 6/1998
(Continued)

OTHER PUBLICATIONS

Machine Translation of JP 2006 339010.*
(Continued)

*Primary Examiner* — J. E. Schoenholtz
(74) *Attorney, Agent, or Firm* — Westerman, Hattori, Daniels & Adrian, LLP

(57) ABSTRACT

An additive for a light-emitting layer contains a compound represented by formula (1):

$$\left[ (A)_m - X(=O)_r \left\{ \begin{matrix} (OR)_n \end{matrix} \right\} \right]_p \quad (1)$$

where X is P, C, or S; A is a cyclic hydrocarbon group that may have H, a direct bond, a chain hydrocarbon group, or a
(Continued)

heteroatom; R is H or an alkyl group, and a plurality of R may link together to form a ring, and if said ring is formed, at least one R is an alkyl group; m is 0 or 1; r is 1 when X is a phosphorous atom or a carbon atom and 2 when X is a sulfur atom; n is a number represented by 3-m when X is a phosphorous atom, and a number represented by 2-m if X is a carbon atom or a sulfur atom; and p is 1 when m is 0, at least 1 when m is 1, and is a substitutable number in A.

34 Claims, 1 Drawing Sheet

(51) Int. Cl.

| | |
|---|---|
| *C07F 5/02* | (2006.01) |
| *C07F 9/11* | (2006.01) |
| *C08K 5/10* | (2006.01) |
| *C08K 5/19* | (2006.01) |
| *C08K 5/3445* | (2006.01) |
| *C08K 5/42* | (2006.01) |
| *C08K 5/49* | (2006.01) |
| *C08K 5/521* | (2006.01) |
| *C08L 65/00* | (2006.01) |
| *H01L 51/50* | (2006.01) |
| *C07C 69/78* | (2006.01) |
| *C07C 69/80* | (2006.01) |
| *C07C 69/96* | (2006.01) |
| *C07C 309/73* | (2006.01) |
| *C07D 317/36* | (2006.01) |
| *C09K 11/06* | (2006.01) |

(52) U.S. Cl.
CPC .......... *C07C 309/73* (2013.01); *C07D 317/36* (2013.01); *C07F 5/022* (2013.01); *C07F 9/11* (2013.01); *C07F 9/5407* (2013.01); *C08K 5/10* (2013.01); *C08K 5/19* (2013.01); *C08K 5/3445* (2013.01); *C08K 5/42* (2013.01); *C08K 5/49* (2013.01); *C08K 5/521* (2013.01); *C08L 65/00* (2013.01); *C09K 11/06* (2013.01); *H01L 51/0038* (2013.01); *H01L 51/0039* (2013.01); *H01L 51/0043* (2013.01); *H01L 51/0065* (2013.01); *H01L 51/50* (2013.01); *C08G 2261/124* (2013.01); *C08G 2261/3142* (2013.01); *C08G 2261/3422* (2013.01); *C08G 2261/5222* (2013.01); *C08G 2261/95* (2013.01); *C09K 2211/1416* (2013.01); *C09K 2211/1425* (2013.01); *H01L 51/5032* (2013.01)

(56) References Cited

U.S. PATENT DOCUMENTS

| | | | | |
|---|---|---|---|---|
| 5,861,224 | A * | 1/1999 | Barker | C07C 69/96 429/306 |
| 5,965,281 | A * | 10/1999 | Cao | H01L 51/0038 257/40 |
| 7,887,876 | B2 * | 2/2011 | Cao | H01L 51/5092 427/66 |
| 8,592,614 | B2 | 11/2013 | Becker et al. | |
| 2002/0177039 | A1 * | 11/2002 | Lu | H01G 9/035 429/213 |
| 2006/0255332 | A1 | 11/2006 | Becker et al. | |
| 2008/0224089 | A1 * | 9/2008 | Pei | H01L 51/0006 252/62.2 |
| 2012/0019161 | A1 | 1/2012 | Edman et al. | |
| 2012/0043530 | A1 * | 2/2012 | Badre | H01B 1/122 257/40 |
| 2012/0049120 | A1 * | 3/2012 | Chen | C09D 11/10 252/301.35 |
| 2013/0006118 | A1 * | 1/2013 | Pan | A61N 5/0616 600/476 |
| 2014/0091295 | A1 | 4/2014 | Becker et al. | |
| 2016/0312006 | A1 * | 10/2016 | Badre | C08L 65/00 |
| 2017/0338060 | A1 * | 11/2017 | Vermeulen | H01G 11/60 |
| 2018/0138453 | A1 * | 5/2018 | Burroughes | H01L 51/5032 |
| 2018/0327622 | A1 * | 11/2018 | Pan | C09D 11/033 |

FOREIGN PATENT DOCUMENTS

| | | | |
|---|---|---|---|
| JP | 2006-339010 | A | 12/2006 |
| JP | 2006339010 | A * | 12/2006 |
| JP | 2006339010 | A * | 12/2006 |
| JP | 2011-103234 | A | 5/2011 |
| JP | 2013-522816 | A | 6/2013 |
| WO | 2005/003253 | A2 | 1/2005 |
| WO | 2010/085180 | A1 | 7/2010 |

OTHER PUBLICATIONS

Mindemark, J., and L. Edman. "Illuminating the Electrolyte in Light-Emitting Electrochemical Cells." Journal of Materials Chemistry C, vol. 4, No. 3, 2016, pp. 420-432., doi:10.1039/c5tc03429a.*
Meier, Sebastian B., et al. "Light-Emitting Electrochemical Cells: Recent Progress and Future Prospects." Materials Today, vol. 17, No. 5, 2014, pp. 217-223., doi:10.1016/j.mattod.2014.04.029.*
Methyl Ester Sulfonate the Next Generation Surfactant, Chemithon, CESIO 2008.*
Han et al., "Light-Emitting Electrochemical Cell (LEC) Using Polythiophene Derivative," Molecular Crystals and Liquid Crystals, Sep. 2000, vol. 349, pp. 467-470 (7 pages, including publisher information and cover pp.), cited in ISR.
International Search Report dated Oct. 18, 2016, issued in counterpart International Application No. PCT/JP2016/071490 (2 pages).
Extended (supplementary) European Search Report dated Aug. 21, 2018, issued in counterpart European Application No. 16830433.5. (7 pages).

* cited by examiner

Figure 1
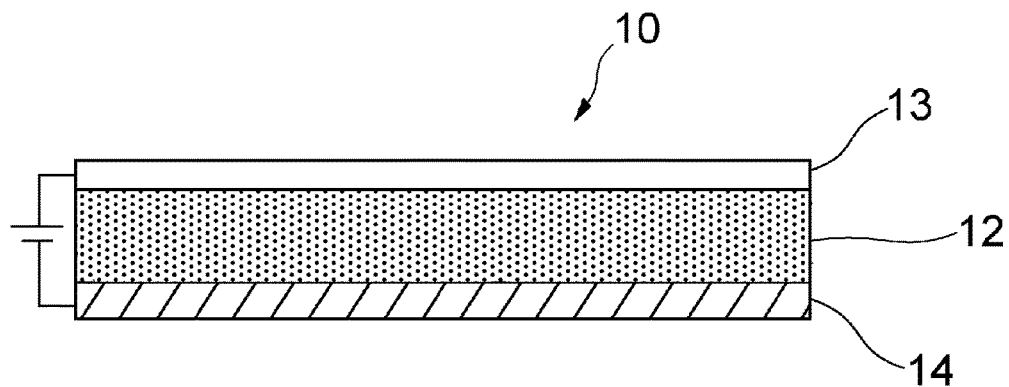
Figure 2(a)            Figure 2(b)
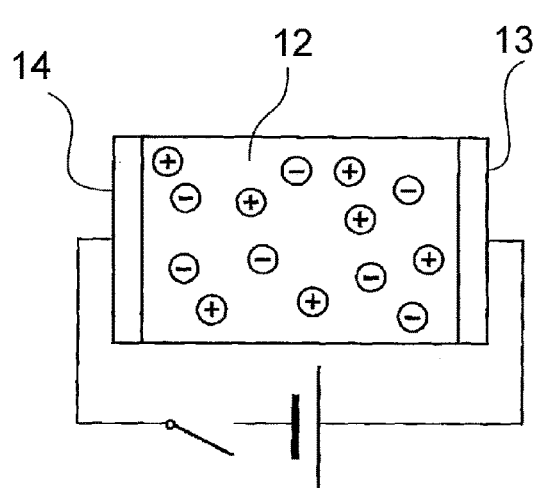 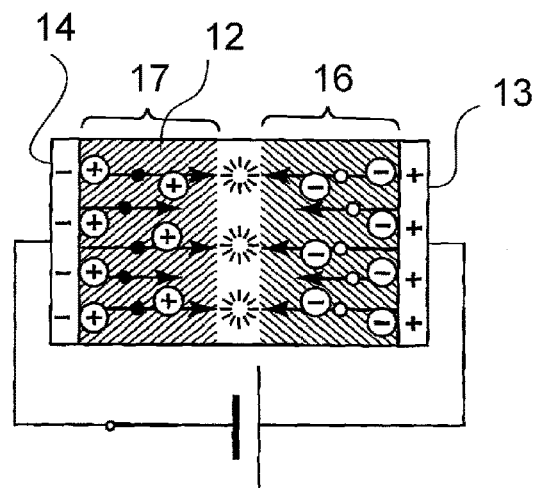

ADDITIVE FOR LIGHT-EMITTING LAYER IN LIGHT-EMITTING ELECTROCHEMICAL CELL, COMPOSITION FOR FORMING LIGHT-EMITTING LAYER IN LIGHT-EMITTING ELECTROCHEMICAL CELL, AND LIGHT-EMITTING ELECTROCHEMICAL CELL

TECHNICAL FIELD

The present invention relates to an additive for a light-emitting layer in a light-emitting electrochemical cell. The present invention relates also to a composition for forming a light-emitting layer of a light-emitting electrochemical cell. The present invention relates further to a light-emitting electrochemical cell using an additive for a light-emitting layer.

BACKGROUND ART

In recent years, there are drastically progressing developments of organic electroluminescent (organic EL) devices which are self-luminous devices with electrons and holes as carriers. Organic EL has features of being capable of achieving more thickness reduction and weight reduction and being better in visibility than liquid crystal devices, which necessitate backlights and are non-self-luminous.

The organic EL devices usually have a pair of substrates on surfaces facing each other of which respective electrodes are formed, and a light-emitting layer disposed between the pair of substrates. Among these, the light-emitting layer is composed of an organic thin film containing a light-emitting material to emit light by application of a voltage. When such organic EL devices are made to emit light, holes and electrons are injected by applying a voltage from an anode and a cathode to the organic thin film. Thereby, light emission can be obtained due to that holes and electrons are caused to be recombined in the organic thin film and excitons produced by the recombination return to their ground state.

In the organic EL devices, in addition to the light-emitting layer, a hole injection layer and an electron injection layer to raise the injection efficiency of holes and electrons, and a hole transport layer and an electron transport layer to improve the recombination efficiency of holes and electrons, respectively, must be provided between the light-emitting layer and the electrodes. Hence, the organic EL devices come to have a multilayer structure, making the structure complex and increasing the number of the production processes. Further the organic EL devices have many restrictions, since the work functions must be taken into consideration in selection of electrode materials to be used for anodes and cathodes.

As self-luminous devices coping with these problems, light-emitting electrochemical cells (LECs) have recently attracted attention (Patent Literatures 1 and 2). The light-emitting electrochemical cells generally have a light-emitting layer containing an ionic compound and a light-emitting material. As the ionic compound, various types of inorganic salts and organic salts are used; and as the light-emitting material, organic polymers, metal complexes and the like are used. In the voltage application, cations and anions originated from the ionic compound migrate in the light-emitting layer toward a cathode and an anode, respectively, and make large electric field gradients (electric double layers) at electrode interfaces. Since the formed electric double layers facilitate injection of electrons and holes at the cathode and anode, respectively, the light-emitting electrochemical cells have no need of having a multilayer structure as in organic EL. Further since the work functions of materials to be used as cathodes and anodes are not required to be taken into consideration for the light-emitting electrochemical cells, there are few restrictions on the materials. For these reasons, the light-emitting electrochemical cells are expected as self-luminous devices capable of reducing the production cost more largely as compared with the organic EL.

CITATION LIST

Patent Literature

Patent Literature 1: Japanese Patent Laid-Open No. 2011-103234
Patent Literature 2: International Publication No. WO 2010/085180

SUMMARY OF INVENTION

Technical Problem

As light-emitting materials having been used for light-emitting layers of conventional light-emitting electrochemical cells, organic polymeric light-emitting materials similar to light-emitting materials having been used for organic EL, particularly π-conjugated polymers are often used. The organic polymers function as light-emitting materials, and besides simultaneously have functions of transporting holes and electrons. Thin films using the organic polymeric light-emitting material as a light-emitting material, though having high mobilities of holes and electrons, pose a problem that the mobility of ions (called also the transportability of ions) is low. On the other hand, combinations of a luminous substance of a metal complex, an organic low-molecular material, a quantum dot material or the like with an organic polymeric conductive material to transport holes and electrons to the luminous substance are sometimes used, and also in this case, a low ion mobility is considered to be a problem.

A cause of the low ion mobility in light-emitting layers of the light-emitting electrochemical cells is said to be low compatibility of a light-emitting material having a low polarity (in detail, an organic polymeric light-emitting material when the organic polymeric light-emitting material is used as the light-emitting material, and an organic polymeric conductive material when a combination of a metal complex, an organic low-molecular material, a quantum dot material or the like with the organic polymeric conductive material is used as the light-emitting material) with an ionic compound having a high polarity. The low ion mobility, particularly the low ion mobility due to the low compatibility of a light-emitting material with an ionic compound, results in reduction in the re-orientation velocity at the above-mentioned electrode interfaces and also reduction in the injection efficiency of holes and electrons.

For the purpose of enhancing the compatibility of a light-emitting material with an ionic compound and raising the ion mobility in a light-emitting layer, also in Patent Literatures 1 and 2, there are descriptions of using, as the ionic compound, an ionic liquid being an organic salt in place of inorganic salts conventionally used, adding a polymeric compound such as a polyethylene oxide, and the like.

However, developments of technologies capable of further improving the compatibility of light-emitting materials with ionic compounds have been awaited.

Solution to Problem

As a result of exhaustive studies to solve the above-mentioned problems, the present inventors have found that addition of a specific compound having an ester bond to a light-emitting layer containing a light-emitting material and an ionic compound can improve the compatibility between the both in a variety of combinations of light-emitting materials with ionic compounds, and can achieve an improvement in the film quality of an organic thin film to form the light-emitting layer, and these findings have led to the completion of the present invention.

That is, the present invention has solved the above problems by providing an additive, comprising a compound represented by the following general formula (1), for a light-emitting layer of a light-emitting electrochemical cell.

[Formula 1]

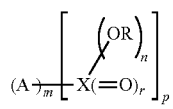

(1)

wherein X is a phosphorus atom, a carbon atom or a sulfur atom;

A is a hydrogen atom, a direct bond, an aromatic hydrocarbon group, a chain aliphatic hydrocarbon group, an alicyclic hydrocarbon group or a heterocyclic group;

R is a hydrogen atom or a branched-chain, straight-chain or cyclic alkyl group; when a plurality of R are present, they may be identical or different; the plurality of R bonded to the same X through O may be linked mutually and form a ring; and when the ring is not formed, at least one R is an alkyl group;

m is 0 or 1;

r is 1 when X is a phosphorus atom or a carbon atom, and is 2 when X is a sulfur atom;

n is a number represented by 3-m when X is a phosphorus atom, and is a number represented by 2-m when X is a carbon atom or a sulfur atom;

p is 1 when m is 0 or when m is 1 and A is a hydrogen atom, is 2 when m is 1 and A is a direct bond, and is a substitutable number on A when m is 1 and A is not a hydrogen atom or a direct bond; and provided that if X is a phosphorus atom or a sulfur atom, A is not a direct bond; and if X is a sulfur atom, A is not a hydrogen atom.

Further the present invention has solved the above problems by providing a composition, comprising a compound represented by the above general formula (1), an ionic compound and a light-emitting material, for forming a light-emitting layer of a light-emitting electrochemical cell.

Further the present invention has solved the above problems by providing a light-emitting electrochemical cell comprising a light-emitting layer and an electrode disposed on each surface thereof, wherein the light-emitting layer comprises a light-emitting material, an ionic compound and a compound represented by the above general formula (1).

Advantageous Effects of Invention

The present invention, if an additive is added to a light-emitting layer in a light-emitting electrochemical cell, provides the additive capable of providing the light-emitting layer high in the luminous efficiency and excellent in the emission luminance. There is further provided a composition for forming a light-emitting layer high in the luminous efficiency and excellent in the emission luminance. There is also provided a light-emitting electrochemical cell using the additive or the composition for forming a light-emitting layer as its light-emitting layer.

BRIEF DESCRIPTION OF DRAWINGS

FIG. 1 is a schematic cross-sectional view of a light-emitting electrochemical cell in one embodiment of the present invention.

FIGS. 2(a) and 2(b) each is a conceptual view illustrating a light emission mechanism of a light-emitting electrochemical cell. FIG. 2(a) illustrates the light-emitting electrochemical cell before a voltage application, and FIG. 2(b) illustrates the light-emitting electrochemical cell after the voltage application.

DESCRIPTION OF EMBODIMENTS

Hereinafter, preferred embodiments according to the present invention will be described.

First, one embodiment of a light-emitting electrochemical cell being an object to which an additive of the present invention is added will be described based on the drawings. As illustrated in FIG. 1, a light-emitting electrochemical cell 10 to be used in the present embodiment has a light-emitting layer 12, and electrodes 13, 14 disposed on each surface thereof. The light-emitting electrochemical cell 10 has the first electrode 13 and the second electrode 14 being a pair of electrodes facing each other, and the light-emitting layer 12 interposed between the pair of electrodes 13, 14. The light-emitting electrochemical cell 10 is so configured that the light-emitting layer emits light by application of a voltage. The light-emitting electrochemical cell 10 is one to be used as various types of displays and the like. FIG. 1 illustrates such a state that a direct current power source is used as a power source; and the first electrode 13 is connected to a positive pole of the direct current power source, and the second electrode 14 is connected to a negative pole thereof. However, contrary to the illustration, the first electrode 13 may be connected to the negative pole, and the second electrode 14 may be connected to the positive pole. Further, in place of the direct current power source as the power source, an alternating current power source may also be used.

The first electrode 13 and the second electrode 14 may be transparent electrodes having light transmissivity, or may be translucent or opaque electrodes. The transparent electrodes having light transmissivity include those composed of a metal oxide such as an indium-doped tin oxide (ITO) or a fluorine-doped tin oxide (FTO), and further include those composed of a polymer having transparency, such as an impurity-added poly(3,4-ethylenedioxythiophene) (PEDOT). Examples of the translucent or opaque electrodes include metallic materials such as aluminum (Al), silver (Ag), gold (Au), Platinum (Pt), tin (Sn), bismuth (Bi), copper (Cu) and chromium (Cr).

It is preferable that at least one of the first electrode 13 and the second electrode 14 is made as a transparent electrode, because light emitted from the light-emitting layer 12 can easily be extracted outside. Further it is preferable that one thereof be made as a transparent electrode and the other thereof is made as an opaque metal electrode, because light emitted from the light-emitting layer 12 can be extracted outside while being reflected from the metal electrode. Further both of the first electrode 13 and the second electrode 14 may also be made as transparent electrodes to make a see-through emitter. Further by making both of the first electrode 13 and the second electrode 14 as metal electrodes composed of Ag or the like, which is a material having a high reflectance, and by regulating the film thickness of the light-emitting layer 12, the light-emitting electrochemical cell 10 can also be made to be a laser oscillating device.

When the first electrode 13 is made as a transparent electrode and the second electrode 14 is made as an opaque or translucent metal electrode, the first electrode 13 preferably has a thickness of, for example, 10 nm or larger and 500 nm or smaller from the viewpoint of realizing a suitable resistivity and light transmissivity. The second electrode 14 preferably has a thickness of, for example, 10 nm or larger and 500 nm or smaller from the viewpoint of realizing a suitable resistivity and light transmissivity as in the first electrode 13.

The light-emitting layer 12 is made by mixing a light-emitting material and an ionic compound. The light-emitting layer 12 may be in either of a solid state and a liquid state. It is preferable that the light-emitting layer 12 is in a solid state, because the light-emitting layer can maintain its constant shape and resist to a force applied from outside; and by combining flexible materials, for example, flexible electrodes with the light-emitting layer 12, a flexible light-emitting electrochemical cell can be fabricated.

In the present invention, the light-emitting material refers to one which functions as carriers of electrons and holes (having transport functions of holes and electrons) by being doped with an anion and a cation, and excites and emits light (having a light-emitting function) by combination of electrons and holes. Therefore, in the present invention, the expression called simply "light-emitting material" means a conductive light-emitting material. In the present invention, the light-emitting material may be a material having both the transport functions of holes and electrons and the light-emitting function, or may be a combination of a material having the transport functions of holes and/or electrons with a material to receive holes and electrons from the former material and emit light.

In the former case, the material having both the transport functions of holes and electrons and the light-emitting function includes organic polymeric light-emitting materials described later. Then in the latter case, the material having the transport functions of holes and/or electrons includes organic polymeric conductive materials such as polyvinylcarbazole described later. Then as the material having the functions to receive holes and electrons from the material transporting holes and/or electrons and emit light, materials other than organic polymers are usually used, and the materials include metal complexes, organic low-molecular materials and quantum dot materials described later. In the present description, also an organic polymeric conductive material having no light-emitting function or a low light-emitting function, in the case of being used as a combination with a light-emitting material other than an organic polymer such as a metal complex, an organic low-molecular material or a quantum dot material, is thus included in a "light-emitting material". Therefore, for example, the "compatibility with the light-emitting material" described later, in the case of using, as a light-emitting material, a combination of the organic polymeric conductive material with the metal complex, organic low-molecular material or quantum dot material, includes the compatibility with the conductive material in the light-emitting material.

In the present embodiment, in the light-emitting layer 12, in addition to a light-emitting material and an ionic compound, a specific additive is incorporated. The additive of the present embodiment comprises a compound represented by the following general formula (1).

[Formula 2]

(1)

wherein X is a phosphorus atom, a carbon atom or a sulfur atom;

A is a hydrogen atom, a direct bond, an aromatic hydrocarbon group, a chain aliphatic hydrocarbon group, an alicyclic hydrocarbon group or a heterocyclic group;

R is a hydrogen atom or a branched-chain, straight-chain or cyclic alkyl group; when a plurality of R are present, they may be identical or different; the plurality of R bonded to the same X through O may be linked mutually and form a ring; and when the ring is not formed, at least one R is an alkyl group;

m is 0 or 1;

r is 1 when X is a phosphorus atom or a carbon atom, and is 2 when X is a sulfur atom;

n is a number represented by 3-m when X is a phosphorus atom, and is a number represented by 2-m when X is a carbon atom or a sulfur atom;

p is 1 when m is 0 or when m is 1 and A is a hydrogen atom, is 2 when m is 1 and A is a direct bond, and is a substitutable number on A when m is 1 and A is not a hydrogen atom or a direct bond; and provided that if X is a phosphorus atom or a sulfur atom, A is not a direct bond; and if X is a sulfur atom, A is not a hydrogen atom.

As in the above general formula (1), the additive to be used in the present invention comprises a compound having an ester bond(s) being a group represented by $[-X(=O)_r(-O-)_n]$. As a result of studies by the present inventors, it has been found that the addition of the compound having a specific structure having an ester bond(s) unexpectedly enables enhancing the compatibility (referred to also as dispersibility) of the light-emitting material with the ionic compound. As a result, since the emission luminance of the light-emitting electrochemical cell can be raised at a low voltage, a high luminance can be achieved while the electric power consumption is suppressed.

The present inventors presume the reason therefor to be as follows. In the above specific structure of the general formula (1), the ester bond moiety represented by $[-X(=O)_r(-O-)_n]$ has a polarity, and an alkyl group(s) represented by R or the alkyl group(s) and a group(s) represented by A become low-polarity sites. Then, when an additive comprising a compound of the general formula (1) is added to the light-emitting layer having the light-emitting material and the ionic compound, since the low-polarity sites in the compound have a high compatibility with the light-emitting material, the additive is easily dispersed in the light-emitting layer. Further since the polar moiety of the compound of the general formula (1) dispersed in the light-emitting material has a high compatibility with the ionic compound, the compatibility of the light-emitting material with the ionic compound, or the dispersibility of the ionic compound in the light-emitting material can be enhanced. Such enhancement of the dispersibility of the ionic compound in the light-emitting material improves the transportability of ions and additionally makes the compound of the general formula (1) dispersed in the light-emitting material to be migratory points of the ionic compound to thereby impart the transportability of ions to the light-emitting material. For the above reason, it is conceivable that when the additive of the present invention is added to the light-emitting layer, the emission luminance of the light-emitting electrochemical cell can be raised at a low voltage since the transportability of ions in the light-emitting layer is enhanced.

In the present description, the ester bond includes any of a phosphate ester bond, a phosphonate ester bond, a carbonate ester bond, carboxylate ester bond and a sulfate ester bond. p being the number of the ester bond in the general formula (1) is 1 when m is 0 or m is 1 and A is a hydrogen atom, and is 2 when m is 1 and A is a direct bond provided that X is a carbon atom. When m is 1 and A is an aromatic hydrocarbon group, a chain aliphatic hydrocarbon group, an alicyclic hydrocarbon group or a heterocyclic group, however, p may be the number of groups substitutable on these groups represented by A. A preferable upper limit of the number of p when m is 1 and A is an aromatic hydrocarbon group, a chain aliphatic hydrocarbon group, an alicyclic hydrocarbon group or a heterocyclic group is preferably 6 or smaller, and more preferably 4 or smaller, for example, from the viewpoint of the compatibility of the compound represented by the general formula (1) with the light-emitting material, and from the viewpoint of availability of the compound represented by the general formula (1). Further a preferable lower limit of the number of p when m is 1 and A is an aromatic hydrocarbon group, a chain aliphatic hydrocarbon group, an alicyclic hydrocarbon group or a heterocyclic group is preferably 1 or larger, from the viewpoint of the compatibility of the compound represented by the general formula (1) with the ionic compound, and from the viewpoint of availability of the compound represented by the general formula (1).

Examples of the aromatic hydrocarbon group represented by A in the general formula (1) include groups obtained by removing one hydrogen atom on an aromatic ring in an aromatic hydrocarbon compound, that is, aryl groups. Specific examples of the aromatic hydrocarbon group include a phenyl group, a naphthyl group, an anthracenyl group and groups obtained by replacing one or two or more hydrogen atoms bonded to these aromatic rings with a chain aliphatic hydrocarbon group(s), for example, a tolyl group or a xylyl group. The aromatic hydrocarbon group has preferably 6 or more and 22 or less carbon atoms, and more preferably 6 or more and 14 or less carbon atoms, in consideration of the compatibility of the compound represented by the general formula (1) with the light-emitting material and the ionic compound. The number of carbon atoms mentioned herein, when the aromatic rings are substituted with chain aliphatic hydrocarbon groups, includes the number of carbon atoms of the chain aliphatic hydrocarbon groups. Examples of the chain aliphatic hydrocarbon groups include groups exemplified as chain aliphatic hydrocarbon groups represented by A described later.

The chain aliphatic hydrocarbon groups represented by A in the general formula (1) include chain saturated aliphatic hydrocarbon groups and chain unsaturated hydrocarbon groups. The chain saturated aliphatic hydrocarbon groups include branched-chain or straight-chain alkyl groups such as a methyl group, an ethyl group, an n-propyl group, an isopropyl group, an n-butyl group, an s-butyl group, a t-butyl group, an isobutyl group, an n-amyl group, an isoamyl group, a t-amyl group, an n-hexyl group, an n-heptyl group, an isoheptyl group, a t-heptyl group, an n-octyl group, an isooctyl group, a 2-ethylhexyl group, a t-octyl group, a nonyl group, an isononyl group, a decyl group, an isodecyl group, an undecyl group, a dodecyl group, a tridecyl group, an isotridecyl group, a tetradecyl group, a hexadecyl group, an octadecyl group and an icosyl group. The chain unsaturated aliphatic hydrocarbon groups include groups obtained by replacing one or more carbon-carbon single bonds in the chain saturated aliphatic hydrocarbon groups with carbon-carbon double bonds or triple bonds, and include, for example, alkenyl groups and alkynyl groups. The alkenyl groups include straight-chain or branched-chain alkenyl groups such as a vinyl group, an allyl group, an isopropenyl group, a 2-butenyl group, a 2-methylallyl group, a 1,1-dimethylallyl group, a 3-methyl-2-butenyl group, a 3-methyl-3-butenyl group, 4-pentenyl group, a hexenyl group, an octenyl group, a nonenyl group and a decenyl group. Examples of the alkynyl groups include an ethynyl group and a prop-2-yn-1-yl group. The chain aliphatic hydrocarbon groups represented by A have preferably 2 or more and 16 or less carbon atoms, and more preferably 4 or more and 8 or less carbon atoms, in consideration of the compatibility of the compound represented by the general formula (1) with the light-emitting material and the ionic compound, and the like.

The alicyclic hydrocarbon groups represented by A in the general formula (1) include saturated alicyclic hydrocarbon groups and unsaturated alicyclic hydrocarbon groups. The saturated alicyclic hydrocarbon groups include a cyclopentyl group, a cyclohexyl group and groups obtained by replacing one or more hydrogen atoms in these groups with any of the above chain aliphatic hydrocarbon groups. The unsaturated alicyclic hydrocarbon groups include a cyclopentynyl group, a cyclohexynyl group, a cyclohexydienyl group and groups obtained by replacing one or more hydrogen atoms in these groups with any of the above chain aliphatic hydrocarbon groups. These alicyclic hydrocarbon groups represented by A have preferably 4 or more and 20 or less carbon atoms, and more preferably 5 or more and 18 or less carbon atoms, in consideration of the compatibility of the compound represented by the general formula (1) with the light-emitting material and the ionic compound, and the like. The number of carbon atoms mentioned herein, when the aliphatic rings are substituted with chain aliphatic hydrocarbon groups, includes the number of carbon atoms of the chain aliphatic hydrocarbon groups.

Examples of the heterocyclic groups represented by A in the general formula (1) include monovalent groups derived from pyridine, pyrrole, furan, imidazole, pyrazole, oxazole, imidazoline, pyrazine or the like. The heterocyclic groups represented by A have preferably 3 or more and 8 or less carbon atoms, and more preferably 4 or more and 6 or less carbon atoms, in consideration of the compatibility of the compound represented by the general formula (1) with the light-emitting material and the ionic compound, and the like. The number of carbon atoms mentioned herein, when the heterocyclic groups are substituted with chain aliphatic hydrocarbon groups, does not include the number of carbon atoms of the chain aliphatic hydrocarbon groups. The number of carbon atoms of the heterocyclic groups including the number of carbon atoms of the chain aliphatic hydrocarbon groups is preferably 4 or more and 20 or less, and more preferably 6 or more and 16 or less.

In the each group cited above as examples of the groups represented by A in the general formula (1), one or two or more hydrogen atoms contained therein may be replaced with functional groups. Examples of the functional groups include an amino group, a nitrile group, a phenyl group, a benzyl group, a carboxyl group and an alkoxy group having 1 or more and 12 or less carbon atoms. When the above-mentioned aromatic hydrocarbon group, chain aliphatic hydrocarbon group, alicyclic hydrocarbon group or heterocyclic group is substituted with the functional group, the above-mentioned preferable number of carbon atoms for the aromatic hydrocarbon group, the chain aliphatic hydrocarbon group, the alicyclic hydrocarbon group or the heterocyclic group does not include the number of carbon atoms of the functional group.

The alkyl groups represented by R in the general formula (1) may be any of branched-chain, straight-chain and cyclic alkyl groups, but branched-chain and straight-chain alkyl groups are preferable. The branched-chain or straight-chain alkyl groups represented by R include groups cited above as examples of the chain saturated aliphatic hydrocarbon groups represented by A. Further the cyclic alkyl groups represented by R include groups cited above as examples of the saturated alicyclic hydrocarbon groups represented by A.

A plurality of R bonded to the same X through O may be linked mutually and form a ring. Examples of compounds of the general formula (1) in which such two R are linked mutually and form a ring include cyclic carbonates and cyclic phosphates. When the compounds of the general formula (1) have no ring formed by mutual linkage of the plurality of R, it is essential that in the general formula (1), out of R present in the number of n×p, at least one R is an alkyl group. In the general formula (1), the number of R being an alkyl group(s) is preferably 1 or more, and more preferably 2 or more. Therefore, in the case of p=1, out of R in the number of n each bonded to one X through an oxygen atom, preferably one or more R are alkyl groups and more preferably two or more R are alkyl groups. Further in the case of p=2, out of R in the number of n each bonded to one X through an oxygen atom, at least one R is an alkyl group. In the general formula (1), it is especially preferable that the number of R being alkyl groups be 3 or more.

The number of carbon atoms of the alkyl groups represented by R is preferably 16 or smaller, more preferably 14 or smaller, still more preferably 10 or smaller, and especially preferably 8 or smaller, from the viewpoint of maintaining high the compatibility of the additive of the present invention with the ionic compound to securely attain the advantage of the present invention, and from the viewpoint of the solubility to a solvent. Further when the number of carbon atoms of the alkyl groups represented by R is 1 or larger, the advantage of the present invention can be attained sufficiently, but the number is preferably 2 or larger, more preferably 3 or larger, and especially preferably 4 or larger from the viewpoint of easily providing a high luminance at a lower voltage when the additive is added to the light-emitting layer.

In the alkyl groups represented by R and the ring formed by linkage of the plurality of R, one or two or more hydrogen atoms contained therein may be replaced with functional groups. Examples of the functional groups include an amino group and a nitrile group.

In the compounds represented by the general formula (1), it is preferable from the viewpoint of easy availability of the compounds, and the like that X be a phosphorus atom or a carbon atom. Then, it is preferable that X be a phosphorus atom, from the viewpoint of easy availability and easy handleability that p be 1.

Further it is preferable that X be a carbon atom, from the viewpoint of more securely attaining the advantage of providing a high emission luminance at a low voltage that m be 1. From these viewpoints, the compound represented by the general formula (1) to be used is preferably a compound represented by the following general formula (2) or the following general formula (3). The compound represented by the general formula (2) is a phosphate ester, and a compound in which in the general formula (1), X is a phosphorus atom, m is 0, and p is 1. Then, the compound represented by the following general formula (3) is a carboxylate ester, and a compound in which in the general formula (1), X is a carbon atom, and m is 1. In the compound represented by the general formula (3), A is preferably an aromatic hydrocarbon group, a chain aliphatic hydrocarbon group, an alicyclic hydrocarbon group or a heterocyclic group.

[Formula 3]

(2)

wherein R is as defined in the general formula (1).

[Formula 4]

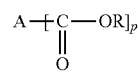

(3)

wherein A, R ad p are as defined in the general formula (1).

Further as the compound represented by the general formula (1), when X is a sulfur atom, a compound represented by the following general formula (a) is preferable from the viewpoint of the voltage withstandability, the compatibility with the light-emitting material, and the like.

[Formula 4A]

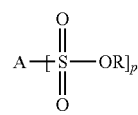

(a)

wherein R and p are as defined in the formula (1); and A is an aromatic hydrocarbon group, a chain aliphatic hydrocarbon group, an alicyclic hydrocarbon group or a heterocyclic group.

Further as the compound represented by the general formula (1), also a compound represented by the general formula (b) in which X is a carbon atom and m is 0 is preferable from the viewpoint of the voltage withstandability and the compatibility with the light-emitting material.

[Formula 4B]

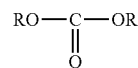

(b)

wherein R is as defined in the general formula (1).

As the compound represented by the above general formula (b), a compound in which either of two R is an alkyl group, and a compound represented by the following general formula (c) in which two R bonded to the same C through O are linked mutually and form a ring are preferable from the viewpoint of the voltage withstandability, the compatibility with the light-emitting material, and the like.

[Formula 4C]

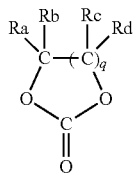

(c)

wherein Ra, Rb, Rc and Rd are a hydrogen atom or an alkyl group, and may be identical or different from one another; and q is the number of 1 or more and 3 or less.

Alkyl groups represented by Ra, Rb, Rc and Rd are preferably straight-chain or branched-chain alkyl groups; and the numbers of carbon atoms of Ra, Rb, Rc and Rd are each preferably 1 or larger and 8 or smaller, and more preferably 1 or larger and 4 or smaller, in consideration of easy availability and easy handleability of the compound. q is preferably the number of 1 or larger and 2 or smaller. A most preferable compound represented by the general formula (c) is a compound in which q is 1, or a compound in which Ra, Rb, Rc and Rd are all hydrogen atoms, or one group in Ra, Rb, Rc and Rd is an alkyl group and the other groups are hydrogen atoms.

The molecular weight of the compound represented by the general formula (1) is preferably 70 or higher and 1,000 or lower, more preferably 120 or higher and 1,000 or lower, especially preferably 150 or higher and 800 or lower, and particularly preferably 200 or higher and 500 or lower; which is preferable from the point that when the compound is added to the light-emitting layer, the luminous efficiency of the light-emitting electrochemical cell is more raised and the emission luminance becomes better. The compound represented by the general formula (1) and the additive of the present invention comprising the compound may be solid or liquid at normal temperature (25° C.).

A production method of the compound represented by the general formula (1) is not especially limited. For example, a phosphate ester compound represented by the general formula (2) can be obtained by dehydration condensation of phosphoric acid with an alcohol, or by condensation of phosphoric acid chloride with an alcohol by the action of a base. Further a carboxylate ester compound represented by the general formula (3) can be obtained by dehydration condensation of a carboxylic acid with an alcohol. A sulfonate ester compound represented by the general formula (a) can be formed, for example, by reaction of a sulfonic acid chloride with an alcohol. A carbonate ester compound represented by the general formula (b) can be produced, for example, by transesterification of dimethyl carbonate with an alcohol. As the compounds represented by the general formula (1), commercially available compounds can also be used.

The additive of the present invention may comprise a compound represented by the general formula (1) alone, or may comprise other components. The other components include solvents and surfactants other than the compounds represented by the general formula (1). The additive of the present invention contains a compound represented by the general formula (1) preferably in 90% by mass or more, more preferably in 95% by mass or more, from the viewpoint of ease of use when being added to the ionic compound and the light-emitting material. A preferable upper limit of the content is 100% by mass.

In the present invention, it is preferable that a compound represented by the general formula (1) be contained in an amount of 1% by mass or larger in the light-emitting layer, because the effect of improving the luminous efficiency and the emission luminance of the light-emitting electrochemical cell can be attained more securely. Further it is preferable that the compound represented by the general formula (1) be contained in an amount of 20% by mass or smaller in the light-emitting layer, from the viewpoint of suppressing a decrease in the emission luminance due to dilution. From these viewpoints, the compound represented by the general formula (1) is contained more preferably in 2% by mass or more and 18% by mass or less, still more preferably in 3% by mass or more and 15% by mass or less, and especially preferably in 5% by mass or more and 10% by mass or less, in the light-emitting layer. The content of the compound represented by the general formula (1) in the light-emitting layer 12 is preferably 2 parts by mass or higher and 30 parts by mass or lower to 100 parts by mass of the light-emitting material. The amount mentioned herein of the light-emitting material is, in the case of using an organic polymeric light-emitting material as the light-emitting material, an amount of the organic polymeric light-emitting material; and in the case of using a combination of a luminous substance such as a metal complex, an organic low-molecular material or a quantum dot material with an organic polymeric conductive material, a total amount of the luminous substance such as the metal complex, the organic low-molecular material or the quantum dot material and the organic polymeric conductive material. The content of the compound represented by the general formula (1) in the light-emitting layer 12 when the light-emitting material is an organic polymeric light-emitting material described later is especially preferably 2 parts by mass or higher and 30 parts by mass or lower to 100 parts by mass of the organic polymeric light-emitting material. When the light-emitting material described later is a combination of a luminous substance such as a metal complex, an organic low-molecular material or a quantum dot material with an organic polymeric conductive material, the content of the compound represented by the general formula (1) in the light-emitting layer 12 is especially preferably 2 parts by mass or higher and 30 parts by mass or lower to 100 parts by mass of the total amount of the luminous substance such as the metal complex, the organic low-molecular material or the quantum dot material, and the organic polymeric conductive material.

Then, the ionic compound will be described. The ionic compound is a substance to make the mobility of ions to be secured, electric double layers to be easily formed and the injection of holes and ions to be facilitated. The ionic compound is a compound having a cation and an anion; and either of a salt of an organic cation and a salt of an inorganic cation can be employed. There can be used, as the salt of an organic cation, a salt whose cation is a phosphonium cation, an ammonium cation, a pyridinium cation, an imidazolium cation, a pyrrolidinium cation or the like. The salts of inorganic cations preferably include salts of cations of I-group or II-group metals. Further the ionic compound may be either of an organic salt and an inorganic salt; the case of organic salts includes the above-mentioned salts of organic cations, and salts composed of an inorganic cation and an organic anion; and in the case of inorganic salts, there can be used salts whose cations are the above-mentioned metal cations, for example, a lithium ion and a potassium ion. Among these, it is preferable that a salt whose cation is at least one selected from a phosphonium cation, an ammonium cation and an imidazolium cation be used, from the viewpoint of the compatibility with the light-emitting material. Particularly when the additive of the present invention is added, from the viewpoint of easily attaining a high luminance at a low voltage, it is preferable to use, as the ionic compound to be used for the light-emitting layer, an ionic compound whose cation is at least one selected from a phosphonium cation and an ammonium cation.

Examples of the ionic compound whose cation is a phosphonium cation or an ammonium cation include compounds represented by the following general formula (4).

[Formula 5]

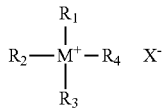

(4)

wherein $R_1$, $R_2$, $R_3$ and $R_4$ each denote an alkyl group, an alkoxyalkyl group, a trialkylsilylalkyl group, an alkenyl group, an alkynyl group, an aryl group or a heterocyclic group, which groups each may be substituted with a functional group; $R_1$, $R_2$, $R_3$ and $R_4$ may be the same or different from one another; M denotes N or P; and $X^-$ denotes an anion.

Examples of the ionic compound whose cation is an imidazolium cation include compounds represented by the following general formula (5).

[Formula 6]

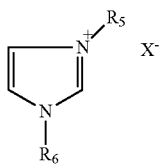

(5)

wherein $R_5$ and $R_6$ each denote an alkyl group, an alkoxyalkyl group, a trialkylsilylalkyl group, an alkenyl group, an alkynyl group, an aryl group or a heterocyclic group, which groups each may be substituted with a functional group; $R_5$ and $R_6$ may be the same or different from each other; and $X^-$ denotes an anion.

The alkyl groups represented by $R_1$, $R_2$, $R_3$, $R_4$, $R_5$ and $R_6$ may be any of branched-chain, straight-chain and cyclic alkyl groups, but branched-chain and straight-chain alkyl groups are preferable. Examples of the branched-chain or straight-chain alkyl groups include groups cited above as the examples of the chain saturated aliphatic hydrocarbon groups represented by A of the above general formula (1). Examples of the cyclic alkyl groups include the groups cited above as the examples of the saturated alicyclic hydrocarbon groups represented by A.

Examples of the alkoxyalkyl groups represented by $R_1$, $R_2$, $R_3$, $R_4$, $R_5$ and $R_6$ include alkoxides of the above-mentioned alkyl groups. Examples of the alkyl groups in the alkoxyalkyl groups include the groups cited above as the examples of the chain saturated aliphatic hydrocarbon groups represented by A of the general formula (1).

Examples of the alkyl groups in the trialkylsilylalkyl groups represented by $R_1$, $R_2$, $R_3$, $R_4$, $R_5$ and $R_6$ include the groups cited above as the examples of the chain saturated aliphatic hydrocarbon groups represented by A of the general formula (1).

The alkenyl groups and the alkynyl groups represented by $R_1$, $R_2$, $R_3$, $R_4$, $R_5$ and $R_6$ include groups cited above as the examples of the alkenyl groups and alkynyl groups represented by A of the general formula (1).

Examples of the aryl groups represented by $R_1$, $R_2$, $R_3$, $R_4$, $R_5$ and $R_6$ include groups cited above as the examples of the aromatic hydrocarbon groups represented by A of the general formula (1). Examples of the heterocyclic groups represented by $R_1$, $R_2$, $R_3$, $R_4$, $R_5$ and $R_6$ include groups cited above as the examples of the heterocyclic groups represented by A of the general formula (1).

In each group cited in the above as groups represented by $R_1$, $R_2$, $R_3$, $R_4$, $R_5$ and $R_6$, one or two or more hydrogen atoms contained therein may be replaced with a functional group(s). Examples of the functional groups include halogen atoms, an amino group, a nitrile group, a phenyl group, a benzyl group, a carboxyl group and alkoxy groups having 1 or more and 12 or less carbon atoms.

In each group cited above as the groups represented by $R_1$, $R_2$, $R_3$, $R_4$, $R_5$ and $R_6$, a part of hydrogen atoms contained therein may be replaced with fluorine atom(s). Introduction of fluorine atoms, since improving the voltage withstandability, leads to the stability and the elongated life of the light-emitting electrochemical cell.

In an ionic compound whose cation is a phosphonium cation or an ammonium cation, from the viewpoint of providing a favorable compatibility with the compound of the general formula (1) and attaining a high luminance, and from the viewpoint of the compatibility with the light-emitting material and the voltage withstandability, one or two or more groups out of $R_1$, $R_2$, $R_3$ and $R_4$ are preferably alkyl groups; and any of $R_1$, $R_2$, $R_3$ and $R_4$ are more preferably alkyl groups. The number of carbon atoms of the alkyl groups represented by $R_1$, $R_2$, $R_3$ and $R_4$ is preferably 2 or more and 18 or less, and more preferably 4 or more and 8 or less, from the viewpoint of more improving the compatibility of the ionic compound with the compound of the general formula (1) and the light-emitting material.

Particularly when two, three or four out of the alkyl groups represented by $R_1$, $R_2$, $R_3$ and $R_4$ are each an alkyl group having the same number of carbon atoms, the number of carbon atoms of the alkyl groups having the same number of carbon atoms is preferably 2 or more and 18 or less, and more preferably 4 or more and 8 or less, from the viewpoint similar to the above.

Further from the viewpoint of more improving the compatibility with the compound of the general formula (1), in the ionic compound whose cation is a phosphonium cation or an ammonium cation, one or more groups out of $R_1$, $R_2$, $R_3$ and $R_4$, particularly three or more groups thereof, are preferably alkyl groups having a difference in the number of carbon atoms of 5 or smaller from the alkyl groups represented by R of the compound represented by the general formula (1). One or more groups out of $R_1$, $R_2$, $R_3$ and $R_4$, particularly three or more groups thereof, are especially preferably alkyl groups having a difference in the number of carbon atoms of 3 or smaller from the alkyl groups represented by R of the compound represented by the general formula (1). In the ionic compound whose cation is a phosphonium cation or an ammonium cation, one or two or more groups out of $R_1$, $R_2$, $R_3$ and $R_4$ are particularly preferably alkyl groups having the same number of carbon atoms as the alkyl groups represented by R of the general formula (1).

When a plurality of compounds represented by the general formula (1) are to be added (or have been added) to the light-emitting layer, the above relation suffices if it is held between the alkyl groups of the cation and R of any one compound of the plurality of compounds. Further when a single compound represented by the formula (1) is to be added (or have been added) to the light-emitting layer, and the compound has a plurality of groups of R, the relation suffices if it is held between the alkyl groups and any one of R.

The molecular weight of the phosphonium cation or the ammonium cation in the general formula (4) is preferably 150 or higher and 750 or lower, especially preferably 200 or higher and 500 or lower, and particularly 250 or higher and 350 or lower; which is preferable because the emission luminance of the light-emitting electrochemical cell is more raised and becomes better.

Further in an ionic compound whose cation is an imidazolium cation, $R_5$ and/or $R_6$ is preferably an alkyl group from the viewpoint of providing a favorable compatibility with the compound represented by the general formula (1) and attaining a high luminance. Further from the viewpoint of attaining a more improvement of the compatibility with the compound represented by the general formula (1) and the light-emitting material, the number of carbon atoms of the alkyl group represented by $R_5$ is preferably 1 or larger and 8 or smaller, and more preferably 1 or larger and 4 or smaller. Further from the viewpoint of attaining a more improvement of the compatibility with the compound represented by the general formula (1) and the light-emitting material, the number of carbon atoms of the alkyl group represented by $R_6$ is preferably 1 or larger and 8 or smaller, and more preferably 2 or larger and 6 or smaller.

In the ionic compound whose cation is an imidazolium cation, from the viewpoint of attaining a more improvement of the compatibility with the compound represented by the general formula (1), $R_6$ is preferably an alkyl group having a difference in the number of carbon atoms of 5 or smaller from the alkyl groups represented by R of the compound represented by the general formula (1) contained in the light-emitting layer, and more preferably an alkyl group having the difference of 3 or smaller. In the ionic compound whose cation is an imidazolium cation, $R_6$ is particularly preferably an alkyl group having the same number of carbon atoms as the alkyl groups represented by R in the general formula (1). Further $R_5$ is preferably an alkyl group having a difference in the number of carbon atoms of 8 or smaller from the alkyl groups represented by R of the compound represented by the general formula (1) contained in the light-emitting layer.

When a plurality of compounds represented by the general formula (1) are to be added (or have been added) to the light-emitting layer, the above relations suffice if it is held between the alkyl groups of the cation and R of any one compound of the plurality of compounds. Further when a single compound represented by the general formula (1) is to be added (or have been added) to the light-emitting layer, and the compound has a plurality of groups of R, the relations suffice if it is held between the alkyl groups and any one of R.

The molecular weight of the imidazolium cation is preferably 90 or higher and 300 or lower, especially preferably 100 or higher and 260 or lower, and particularly 120 or higher and 240 or lower; which is preferable because the emission luminance of the light-emitting electrochemical cell is more raised and becomes better.

In the case of using an ionic compound whose cation is a metal cation, the ionic compound is generally lower in the ion transportability than salts of organic cations. Hence, in order to make a light-emitting electrochemical cell using an ionic compound having a metal cation to smoothly emit light and provide a certain luminance, concurrent use of a polymeric compound such as polyethylene oxide is conventionally needed. In the present invention, however, in the case of using an ionic compound having a metal cation, astonishingly, use of a combination with the additive of the present invention raises the compatibility of the light-emitting material with the ionic compound and attains a certain luminance without using any polymeric compound such as polyethylene oxide. The polymeric compound, such as polyethylene oxide, to be used in order to improve the ion transportability is usually inferior in the voltage withstandability to the additive of the present invention. Hence, use of the additive of the present invention in addition to or as a substitution of the polymeric compound such as polyethylene oxide enables maintaining or improving the voltage withstandability of the light-emitting layer and simultaneously attaining a certain luminance. Although the reason that the additive of the present invention has such an action though not being a polymer is not clear, the present inventors regard, as one cause thereof, that the additive of the present invention can efficiently raise the compatibility of the light-emitting material with the ionic compound, or the dispersibility of the ionic compound in the light-emitting material. The metal ion is preferably a cation of a I-group metal or a II-group metal as described above; and cations of I-group metals preferably include those of Li, Na, K and Cs, and cations of II-group metals preferably include those of Mg and Ca. The metal cations are particularly preferably Li, Na and K from the point of the transportability of ions.

Examples of anions in the above salts of organic cations and inorganic cations and organic salts and inorganic salts, and anions represented by $X^-$ in the above general formulae (5) and (6) include ions of halogens such as fluorine, bromine, iodine and chlorine, tetrafluoroborate ($BF_4$), benzotriazolate ($N_3(C_6H_4)$), tetraphenylborate ($B(C_6H_5)_4$), hexafluorophosphate ($PF_6$), bis(trifluoromethylsulfonyl)imide ($N(CF_3SO_2)_2$), bis(fluorosulfonyl)imide ($N(SO_2F)_2$), trifluoromethanesulfonate ($SO_3CF_3$), methanesulfonate ($SO_3CH_3$), tris(pentafluoroethyl)trifluorophosphate (($C_2H_5)_3PF_3$), trifluoroacetic acid ($CF_3COO$), amino acids, bisoxalatoborate ($B(C_2O_4)_2$), p-toluenesulfonate ($CH_3C_6H_4SO_3$), p-toluenesulfonyl ($CH_3C_6H_4SO_2$), mesitylenesulfonyl (($CH_3)_3C_6H_4SO_2$), dimethylbenzenesulfonyl (($CH_3)_2C_6H_4SO_2$), thiocyanate (SCN), dicyanamide ($N(CN)_2$), hypophosphorous acid, and besides, phosphate esters represented by the following general formula (7), sulfate ester anions represented by the following general formula (8), dithiophosphorous acid represented by the following general formula (9) and aliphatic carboxylic acids represented by the following general formula (10).

$$PO_2(OR_7)_2 \tag{7}$$

wherein $R_7$ is an alkyl group having 1 or more and 20 or less carbon atoms, and two $R_7$ may be the same or different.

$$SO_3(OR_8) \tag{8}$$

wherein $R_8$ is an alkyl group having 1 or more and 20 or less carbon atoms.

$$(R_9O)_2PSS \tag{9}$$

wherein $R_9$ is an alkyl group having 1 or more and 20 or less carbon atoms, and two $R_9$ may be the same or different.

wherein $R_{10}$ is an alkyl group having 1 or more and 20 or less carbon atoms.

As the anion in the ionic compound, an anion containing no halogen atom is preferably used in that a light-emitting electrochemical cell having a high luminance is obtained. This is because an anion containing no halogen atom has a higher compatibility with the light-emitting material than an anion containing a halogen atom. As is clear from the descriptions of Examples 13 to 17 described later, however, also when the additive of the present invention is added to the light-emitting layer containing an ionic compound having an anion containing a halogen atom, an effect of providing a high emission luminance at a lower voltage can be attained.

Particularly when as the anion in the ionic compound, an anion having an ester bond, such as a phosphate ester bond or a sulfate ester bond, is used, since the ionic compound containing the anion becomes better in the compatibility with many light-emitting materials, it is preferable in that a light-emitting electrochemical cell having a higher luminance is easily obtained.

Further from the viewpoint that there can be obtained a light-emitting electrochemical cell having a high compatibility with the additive of the present invention and having a high luminance, there is preferably used, as an anion in the ionic compound, an anion having an alkyl group having a difference in the number of carbon atoms of 5 or smaller from the alkyl groups represented by R of the compound represented by the general formula (1) to be added to the light-emitting layer, and more preferably used an anion having an alkyl group having a difference in the number of carbon atoms of 3 or smaller therefrom. There is particularly preferably used an anion having an alkyl group having the same number of carbon atoms as the alkyl groups represented by any R in any compound represented by the general formula (1) to be added to the light-emitting layer. Therefore, the difference in the number of carbon atoms between $R_7$ to $R_{10}$ of the general formulae (7) to (10) and R in the general formula (1) is preferably in the above range, and the number of carbon atoms of $R_7$ to $R_{10}$ is most preferably the same as that of R.

When a plurality of compounds represented by the general formula (1) are to be added (or have been added) to the light-emitting layer, the above relation suffices if it is held between the alkyl group of the anion and R of any one compound of the plurality of compounds. Further when a single compound represented by the general formula (1) is to be added (or have been added) to the light-emitting layer, and the compound has a plurality of groups of R, the relation suffices if it is held between the alkyl group and any one of R in the compound.

The ionic compound may be solid or liquid at normal temperature (25° C.). The ionic compound makes a solid state or a liquid state depending on the combination of a cation and an anion to be selected and the structure of the cation. In the present invention, the ionic compound can be used singly or in a combination of two or more thereof.

The ionic compound can be produced, for example, as follows. When the cation is a phosphonium ion, an ion liquid in which the anion is a halogen can be obtained by using a quaternary phosphonium halide obtained by reacting a tertiary phosphine compound corresponding to the phosphonium cation concerned with a halogenated hydrocarbon compound. An ion liquid in which the anion component is not a halogen can be obtained by reacting and anion-interchanging the above quaternary phosphonium halide with a metal salt having the anion component. Also if the cation is an ammonium ion, an ion liquid can be obtained similarly by using a quaternary ammonium halide obtained by reacting a tertiary amine compound with a halogenated hydrocarbon compound. When the cation is an imidazolium ion, an ion liquid can be obtained similarly by using an imidazolium halide obtained by reacting an imidazole compound corresponding to the imidazolium cation concerned with a halogenated hydrocarbon compound.

Further, for example, when the cation is a phosphonium or ammonium ion, and the anion is an ionic compound having a phosphate ester bond or a sulfate ester bond, an ionic compound can be obtained by a halogen-free production method, by reacting a tertiary phosphine compound or a tertiary amine compound with a compound represented by $PO(OR_x)_3$ or $SO_2(OR_x)_2$. Here, $R_x$ is an alkyl group having 1 or more and 20 or less carbon atoms.

The content proportion of the ionic compound in the light-emitting layer 12 is preferably 1% by mass or higher and 20% by mass or lower, and more preferably 2% by mass or higher and 10% by mass or lower, from the viewpoint of securing the ion mobility and enhancing the film formability of the light-emitting layer 12. The content of the ionic compound in the light-emitting layer 12 is preferably 1 part by mass or higher and 25 parts by mass or lower to 100 parts by mass of the light-emitting material. The amount mentioned herein of the light-emitting material is, in the case of using an organic polymeric light-emitting material as the light-emitting material, an amount of the organic polymeric light-emitting material, and in the case of using, as the light-emitting material, a combination of a luminous substance such as a metal complex, an organic low-molecular material or a quantum dot material with an organic polymeric conductive material, a total amount of the luminous substance such as the metal complex, the organic low-molecular material or the quantum dot material, and the organic polymeric conductive material. Further when the light-emitting material is an organic polymeric light-emitting material described later, the content of the ionic compound in the light-emitting layer 12 is preferably 1 part by mass or higher and 25 parts by mass or lower to 100 parts by mass of the organic polymeric light-emitting material; and when the light-emitting material is a metal complex, an organic low-molecular material or a quantum dot material and an organic polymeric conductive material, the content of the ionic compound in the light-emitting layer 12 is preferably 1 part by mass or higher and 25 parts by mass or lower to 100 parts by mass of the total amount of the metal complex, the organic low-molecular material or the quantum dot material, and the organic polymeric conductive material.

As described above, specific examples of the light-emitting material contained in the light-emitting layer 12 include organic polymeric light-emitting materials, and combinations of a luminous substance such as a metal complex, an organic low-molecular material or a quantum dot material with an organic polymeric conductive material.

The organic polymeric light-emitting materials include various types of organic polymers being π-conjugated polymers. Specific examples thereof include para-phenylene vinylene, fluorene, 1,4-phenylene, thiophene, pyrrole, para-phenylene sulfide, benzothiazole, biothiophene, and polymers of derivatives in which substituents are incorporated in these, and copolymers containing these. Such substituents include alkyl groups having 1 or more and 20 or less carbon atoms, alkoxy groups having 1 or more and 20 or less carbon atoms, aryl groups having 6 or more and 18 or less carbon atoms, and groups represented by [(—$CH_2CH_2O$—)$_n$ $CH_3$](n is an integer of 1 or more and 10 or less). Further the copolymers include those made by bonding repeating units of two or more polymers among the above-cited π-conjugated polymers. The arrangement of the each repeating unit in the copolymer includes random arrangement, alternating arrangement, block arrangement and combinations thereof. There are especially preferably used fluorene, para-phenylene vinylene, polymers of derivatives in which substituents are incorporated in these, and copolymers containing these. Further as the organic polymeric light-emitting material, commercially available products can also be used. Examples of such commercially available products include a compound available from Solaris Chem Inc., under the name of SOL2412, Poly[(9,9-dioctylfluorenyl-2,7-diyl)-alt-co-(9,9'-spirobifluorene-2,7-diyl)], a compound available from Merck KGaA., under the name of PDY-132, phenylene-substituted poly(para-phenylene vinylene), and a compound available from Sigma-Aldrich Corp., poly[(9,9-di-n-octylfluorenyl-2,7-diyl)-alt-(benzo[2,1,3]thiadiazol-4,8-diyl)].

As the metal complex, there can be used well-known ones conventionally used as light-emitting materials in organic EL, and examples thereof include phosphorescent emitters such as a tris(8-quinolinolate) aluminum complex, a tris(4-methyl-8-quinolinolate) aluminum complex, a bis(8-quinolinolate) zinc complex, a tris(4-methyl-5-trifluoromethyl-8-quinolinolate) aluminum complex, a tris(4-methyl-5-cyano-8-quinolinolate) aluminum complex, a bis(2-methyl-5-trifluoromethyl-8-quinolinolate)[4-(4-cyanophenyl) phenolate] aluminum complex, a bis(2-methyl-5-cyano-8-quinolinolate)[4-(4-cyanophenyl)phenolate]aluminum complex, a tris(8-quinolinolate) scandium complex, and a bis[8-(para-tosyl)aminoquinoline] zinc complex, cadmium complex and Ir complex, and ruthenium complexes having bipyridyl (bpy) or derivatives thereof, or phenanthroline or derivatives thereof, as their ligands.

As the organic low-molecular material, there can be used well-known ones conventionally used as light-emitting materials in organic EL, and examples thereof include fluorescent emitters such as 9,10-diarylanthracene derivatives, pyrene, coronene, perylene, rubrene, 1,1,4,4-tetraphenylbutadiene, 1,2,3,4-tetraphenylcyclopentadiene, pentaphenylcyclopentadiene, poly-2,5-diheptyloxy-para-phenylene vinylene, coumalin-based fluorescent substances, perylene-based fluorescent substances, pyran-based fluorescent substances, anthrone-based fluorescent substances, porphyrin-based fluorescent substances, quinacridone-based fluorescent substances, N,N'-dialkyl-substituted quinacridone-based fluorescent substances, naphthalimide-based fluorescent substances, and N,N'-diaryl-substituted pyrrolopyrrole-based fluorescent substances.

Further Examples of the quantum dot material include Si, Ge, GaN, GaP, CdS, CdSe, CdTe, InP, InN, ZnS, $In_2S_3$, ZnO, CdO and mixtures thereof.

The organic polymeric conductive materials to transport electrons and/or holes include polyvinylcarbazole, polyphenylene, polyfluorene, polyaniline, polythiophene, polypyrrole, polyphenylene vinylene, polythienylene vinylene, polyquinoline, and polyquinoxaline. Further the organic polymeric light-emitting materials described above can also be used because having the transporting functions of electrons and/or holes.

In these light-emitting materials, from the viewpoint of making their function to be sufficiently exhibited, the content proportion thereof in the light-emitting layer 12 is, in the case of using an organic polymeric light-emitting material, preferably 60% by mass or higher and 99% by mass or lower, and more preferably 70% by mass or higher and 98% by mass or lower. Further in the case of using a combination of a luminous substance such as a metal complex, an organic low-molecular material or a quantum dot material with an organic polymeric conductive material, the proportion of the total amount thereof in the light-emitting layer 12 is preferably 60% by mass or higher and 99% by mass or lower, and more preferably 70% by mass or higher and 98% by mass or lower.

Further in the case of using a combination of a luminous substance such as a metal complex, an organic low-molecular material or a quantum dot material with an organic polymeric conductive material, the proportion of the organic polymeric conductive material to 100 parts by mass of the luminous substance such as the metal complex, the organic low-molecular material or the quantum dot material is preferably 5 parts by mass or higher and 25 parts by mass or lower.

The light-emitting layer 12 may comprise substances other than the light-emitting material and the ionic compound. Examples of such substances include surfactants, and polymer components (polystyrene, polymethyl methacrylate (PMMA) and the like) to improve the film formability. Further in the case of using an organic polymeric light-emitting material as the light-emitting material, organic polymeric conductive materials such as polyvinylcarbazole are also included in the other components. The amount of the components (excluding solvent) other than the light-emitting material, the ionic compound and the compound represented by the general formula (1) in the light-emitting layer 12 is made to be, with respect to 100 parts by mass of the whole light-emitting layer 12, preferably 30 parts by mass or smaller, still more preferably 20 parts by mass or smaller, and especially preferably 10 parts by mass or smaller.

Further in the present invention, there may be used polymeric compounds conventionally used to enhance the charge transportability. Such polymeric compounds include compounds having a polyether skeleton, such as polyethylene oxide and polypropylene oxide, compounds having a polyester skeleton, such as polyethylene succinate and poly-β-propiolactone, compounds having a polyamine skeleton, such as polyethyleneimine, and compounds having a polysulfide skeleton, such as polyalkylene sulfide. In the case of using these polymeric compounds in the light-emitting layer, the amount of these polymeric compounds in the light-emitting layer is preferably 50% by mass or smaller, more preferably 40% by mass or smaller, and especially preferably 30% by mass or smaller. In the present invention, the amount may be smaller than that, and no polymeric compound such as polyethylene oxide may be used. That these polymeric compounds are not used in the light-emitting layer refers to, for example, that the amount of these polymeric compounds in the light-emitting layer is 0% by mass.

The film thickness of the light-emitting layer 12 thus constituted is preferably 20 nm or larger and 300 nm or smaller, and more preferably 50 nm or larger and 150 nm or smaller. When the film thickness of the light-emitting layer 12 is in this range, it is preferable from the viewpoint that light emission can be provided sufficiently and efficiently by the light-emitting layer 12, and defects in a predetermined light-emitting portion can be suppressed to thereby prevent short circuit.

A light-emitting electrochemical cell 10 of the present embodiment can be produced, for example, by the following production method. First, a substrate installed with a first electrode 13 is prepared. When the first electrode 13 is formed, for example, of an ITO, the first electrode 13 composed of the ITO on the surface of the substrate can be formed by forming a vapor-deposited film of the ITO in a patterned shape by using a photolithography process or a combination of a photolithography process and a lift-off process on the surface of the glass substrate and the like.

Then, a composition for forming a light-emitting layer of the light-emitting electrochemical cell is prepared by dissolving or dispersing an ionic compound, a light-emitting material and a compound represented by the general formula (1) in an organic solvent. The organic solvent, from the viewpoint of efficiently mixing the ionic compound, the light-emitting material and the compound represented by the general formula (1), and the like, preferably contains at least one organic solvent selected from the group consisting of toluene, benzene, tetrahydrofuran, dimethyl chloride, cyclohexanone, chlorobenzene and chloroform. In this case, the organic solvent can be used only singly or only as a combination of two or more thereof. Alternatively, other organic solvents such as methanol and ethanol may also be used by being mixed therewith, in the range not impairing properties such as solubility of these compounds. That is, the organic solvent to dissolve or disperse the ionic compound, the light-emitting material and the compound represented by the general formula (1) can contain at least one organic solvent selected from the group consisting of toluene, benzene, tetrahydrofuran, dimethyl chloride, cyclohexanone, chlorobenzene and chloroform, and organic solvents other than these.

With respect to the blend ratio (mass ratio) of the ionic compound and the light-emitting material in the composition for forming a light-emitting layer, the former:the latter is preferably 1:4 to 100. Further with respect to the blend ratio (mass ratio) of the compound represented by the general formula (1) and the light-emitting material in the composition for forming a light-emitting layer, the former:the latter is preferably 1:3 to 50. The amount of the light-emitting material mentioned herein is, in the case of using an organic polymeric light-emitting material as the light-emitting material, an amount of the organic polymeric light-emitting material, and in the case of using, as the light-emitting material, a combination of a luminous substance such as a metal complex, an organic low-molecular material or a quantum dot material with an organic polymeric conductive material, a total amount of the luminous substance such as the metal complex, the organic low-molecular material or the quantum dot material and the organic polymeric conductive material. Further it is preferable from the viewpoint of easily forming a light-emitting layer more securely attaining the advantage of the present invention that the proportion of the compound represented by the general formula (1) in the composition for forming a light-emitting layer be 0.0001% by mass or higher and 10% by mass or lower; and 0.0005% by mass or higher and 5% by mass or lower is especially preferable. The composition for forming a light-emitting layer is applied on the first electrode 13 of the substrate by a spin coating method or the like. Thereafter, a coating film formed by this application is dried to evaporate the organic solvent to thereby form a light-emitting layer 12. The preparation of the composition for forming a light-emitting layer and the formation of the light-emitting layer 12 are preferably carried out in an inert gas atmosphere having preferably a moisture rate of 100 ppm or less. The inert gas in this case includes argon, nitrogen and helium.

Then, a second electrode 14 is formed on the formed light-emitting layer 12. In this case, a predetermined patterned electrode is formed on the light-emitting layer 12, for example, by vapor-depositing aluminum (Al) into a film form by a vacuum vapor-deposition process through a mask. The second electrode 14 is thus formed on the light-emitting layer 12. Thereby, a light-emitting electrochemical cell 10 illustrated in FIG. 1 is obtained.

The light-emitting electrochemical cell 10 of the present embodiment emits light by the following emission mechanism. As illustrated in FIGS. 2(*a*) and 2(*b*), a voltage is applied to the light-emitting layer 12 so that the first electrode 13 becomes an anode and the second electrode 14 becomes a cathode. Thereby, ions in the light-emitting layer 12 migrate along an electric field and a layer where anion species gather is formed in the vicinity of the interface with the first electrode 13 in the light-emitting layer 12. On the other hand, a layer where cation species gather is formed in the vicinity of the interface with the second electrode 14 in the light-emitting layer 12. Electric double layers are thus formed on the respective electrodes. Thereby, a p-doped region 16 is spontaneously formed in the vicinity of the first electrode 13 being an anode, and an n-doped region 17 is spontaneously formed in the vicinity of the second electrode 14 being a cathode. Then, these doped regions constitute high-carrier density p-i-n junctions. Thereafter, holes and electrons are injected from the anode and the cathode to the light-emitting material of the light-emitting layer 12, respectively, and recombine in the i-layer. Excitons are produced from the recombined holes and electrons, and return to a ground state to thereby emit light. Light emission from the light-emitting layer 12 can thus be provided. In order to obtain light of a desired wavelength, it suffices if there is selected a light-emitting material having an energy difference (band gap) between the highest occupied molecular orbital and the lowest unoccupied molecular orbital corresponding to the desired wavelength.

According to the additive, the composition for forming a light-emitting layer and the light-emitting electrochemical cell of the present invention using the compound represented by the general formula (1), dispersing the ionic compound and together the compound represented by the general formula (1) in the light-emitting material in the light-emitting layer improves the compatibility of the light-emitting material with the ionic compound and largely improves the mobility of the ionic compound in the light-emitting material, as compared with the case where no compound represented by the general formula (1) is added. Hence, there can be obtained the light-emitting electrochemical cell having a high emission luminance at a low voltage and being suppressed in the resistance rise in a low-resistance state, as compared with the case where no compound represented by the general formula (1) is added.

EXAMPLES

Hereinafter, the present invention will be described in more detail by way of Examples, but the present invention is not limited thereto. A property in the following Examples was measured by the following method.

<Luminous Property>

A first electrode of a light-emitting electrochemical cell is connected to a positive pole of a direct current, and a second electrode thereof is connected to a negative pole thereof; a voltage is applied at a sweeping rate of 1 V/sec up to 15 V, and the maximum value in the luminance during the application was taken as an emission luminance. Further the voltage at this time was measured. The measurement was carried out by using a CS-2000 (manufactured by Konica Minolta, Inc.).

Example 1

A commercially available glass substrate with an ITO film (manufactured by Geomatec Co., Ltd., ITO film thickness: 200 nm) was used as a first electrode 13.

There were used PFO-spiro (poly[(9,9-dioctylfluorenyl-2,7-diyl)-alt-co-(9,9'-spirobifluorene-2,7-diyl)], manufactured by Solaris Chem Inc., model number: SOL2412) as an organic polymeric light-emitting material, a phosphonium phosphate salt indicated in Table 1 as an ionic compound, and an additive being a compound indicated in Table 1; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material:the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 1.

Comparative Example 1-1

A light-emitting electrochemical cell 10 was fabricated by the same method as in Example 1, except for using no additive. The result of a measurement of the luminous property of the obtained light-emitting electrochemical cell 10 is shown in Table 1.

Comparative Examples 1-2 to 1-4

Light-emitting electrochemical cells 10 were fabricated by the same method as in Example 1, except for using additives indicated in Table 1, respectively. The results of measurements of the luminous property of the obtained light-emitting electrochemical cells 10 are shown in Table 1.

TABLE 1

|  | Luminous Property | | | Organic Polymeric Light-Emitting Material | Emission Color | Ionic Compound | |
|---|---|---|---|---|---|---|---|
|  | Emission Luminance ($cd/m^2$) | Voltage (V) | Additive |  |  | Cation | Anion |
| Example 1 | 20,631 | 5.3 | TBP[3] | PFO-spiro[1] | blue | $P(C_4H_9\text{-n})_4^+$ | $PO_2(OC_4H_9\text{-n})_2^-$ |
| Comparative Example 1-1 | 18,060 | 6.7 | none |  |  |  |  |
| Comparative Example 1-2 | 12,659 | 7.6 | N-MP[4] |  |  |  |  |
| Comparative Example 1-3 | 1,888 | 9.3 | DEG-DBE [5] |  |  |  |  |
| Comparative Example 1-4 | 10,537 | 6.2 | γ-BL[6] |  |  |  |  |

[1]PFO-spiro: (poly[(9,9-dioctylfluorenyl-2,7-diyl)-alt-co-(9,9'-spirobifluorene-2,7-diyl)], manufactured by Solaris Chem Inc., model number: SOL2412)
[3]TBP: tributyl phosphate (manufactured by Kanto Chemical Co., Ltd.)
[4]N-MP: N-methylpyrrolidone (manufactured by Tokyo Chemical Industry Co., Ltd.)
[5] DEG-DBE: diethylene glycol dibutyl ether (manufactured by Tokyo Chemical Industry Co., Ltd.)
[6]γ-BL: γ-butyrolactone (manufactured by Kishida Chemical Co., Ltd.)

Example 2-1 to 2-5

A commercially available glass substrate with an ITO film (manufactured by Geomatec Co., Ltd., ITO film thickness: 200 nm) was used as a first electrode 13.

There were used Super Yellow (phenylene-substituted poly(para-phenylene vinylene), manufactured by Merck KGaA, product name: PDY-132) as an organic polymeric light-emitting material, a phosphonium phosphate salt indicated in Table 2 as an ionic compound, and an additive being a compound indicated in Table 2; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material:the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 2.

Comparative Example 2-1

A light-emitting electrochemical cell 10 was fabricated by the same method as in Example 2-1 to 2-5, except for using no additive. The result of a measurement of the luminous property of the obtained light-emitting electrochemical cell 10 is shown in Table 2.

Comparative Examples 2-2 to 2-4

Light-emitting electrochemical cells 10 were fabricated by the same method as in Example 2-1 to 2-5, except for using additives indicated in Table 2, respectively. The results of measurements of the luminous property of the obtained light-emitting electrochemical cells 10 are shown in Table 2.

TABLE 2

| | Luminous Property | | | Organic Polymeric | | Ionic Compound | |
|---|---|---|---|---|---|---|---|
| | Emission Luminance | Voltage | | Light-Emitting | Emission | | |
| | (cd/m$^2$) | (V) | Additive | Material | Color | Cation | Anion |
| Example 2-1 | 23,323 | 3.9 | TMP[7] | Super Yellow[2] | yellow | P(C$_4$H$_9$-n)$_4$$^+$ | PO$_2$(OC$_4$H$_9$-n)$_2$$^-$ |
| Example 2-2 | 20,733 | 3.6 | TEP[8] | | | | |
| Example 2-3 | 25,477 | 3.5 | TBP[3] | | | | |
| Example 2-4 | 22,977 | 3.4 | THP[9] | | | | |
| Example 2-5 | 22,977 | 3.4 | DBP[10] | | | | |
| Comparative Example 2-1 | 17,570 | 4.1 | none | | | | |
| Comparative Example 2-2 | 15,674 | 3.6 | N-MP[4] | | | | |
| Comparative Example 2-3 | 16,444 | 3.0 | DEG-DBE [5] | | | | |
| Comparative Example 2-4 | 16,695 | 2.3 | γ-BL[6] | | | | |

[2] Super Yellow: (phenylene-substituted poly(para-phenylene vinylene), manufactured by Merck KGaA, product name: PDY-132)
[3] TBP: tributyl phosphate (manufactured by Kanto Chemical Co., Ltd.)
[4] N-MP: N-methylpyrrolidone (manufactured by Tokyo Chemical Industry Co., Ltd.)
[5] DEG-DBE: diethylene glycol dibutyl ether (manufactured by Tokyo Chemical Industry Co., Ltd.)
[6] γ-BL: γ-butyrolactone (manufactured by Kishida Chemical Co., Ltd.)
[7] TMP: trimethyl phosphate (manufactured by Kanto Chemical Co., Ltd.)
[8] TEP: triethyl phosphate (manufactured by Kanto Chemical Co., Ltd.)
[9] THP: trihexyl phosphate (manufactured by Kanto Chemical Co., Ltd.)
[10] DBP: dibutyl phosphate (manufactured by Kanto Chemical Co., Ltd.)

Example 3

A light-emitting electrochemical cell 10 was fabricated by the same method as in Example 1, except for using an ammonium phosphate salt indicated in Table 3 as an ionic compound. The result of a measurement of the luminous property of the obtained light-emitting electrochemical cell 10 is shown in Table 3.

Comparative Example 3

A light-emitting electrochemical cell 10 was fabricated by the same method as in Example 3, except for using no additive. The result of a measurement of the luminous property of the obtained light-emitting electrochemical cell 10 is shown in Table 3.

TABLE 3

| | Luminous Property | | | Organic Polymeric | | Ionic Compound | |
|---|---|---|---|---|---|---|---|
| | Emission Luminance | Voltage | | Light-Emitting | Emission | | |
| | (cd/m$^2$) | (V) | Additive | Material | Color | Cation | Anion |
| Example 3 | 1,110 | 12.0 | TBP[3] | PFO-spiro[1] | blue | N(C$_4$H$_9$-n)$_3$(CH$_3$)$^+$ | PO$_2$(OC$_4$H$_9$-n)$_2$$^-$ |
| Comparative Example 3 | 898 | 13.0 | none | | | | |

[1] PFO-spiro: (poly[(9,9-dioctylfluorenyl-2,7-diyl)-alt-co-(9,9'-spirobifluorene-2,7-diyl)], manufactured by Solaris Chem Inc., model number: SOL2412)
[3] TBP: tributyl phosphate (manufactured by Kanto Chemical Co., Ltd.)

Example 4-1 to 4-4

A commercially available glass substrate with an ITO film (manufactured by Geomatec Co., Ltd., ITO film thickness: 200 nm) was used as a first electrode 13.

There were used Super Yellow (phenylene-substituted poly(para-phenylene vinylene), manufactured by Merck KGaA, product name: PDY-132) as an organic polymeric light-emitting material, an ammonium phosphate salt indicated in Table 4 as an ionic compound, and an additive being a compound indicated in Table 4; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material:the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 4.

Comparative Example 4

A light-emitting electrochemical cell 10 was fabricated by the same method as in Example 4-1 to 4-4, except for using no additive. The result of a measurement of the luminous property of the obtained light-emitting electrochemical cell 10 is shown in Table 4.

Example 5-1 to 5-7

A commercially available glass substrate with an ITO film (manufactured by Geomatec Co., Ltd., ITO film thickness: 200 nm) was used as a first electrode 13.

There were used PFO-spiro (poly[(9,9-dioctylfluorenyl-2,7-diyl)-alt-co-(9,9'-spirobifluorene-2,7-diyl)], manufactured by Solaris Chem Inc., model number: SOL2412) as an organic polymeric light-emitting material, a imidazolium phosphate salt indicated in Table 5 as an ionic compound, and an additive being a compound indicated in Table 5; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material:the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 5.

Comparative Example 5

A light-emitting electrochemical cell 10 was fabricated by the same method as in Example 5-1 to 5-7, except for using no additive. The result of a measurement of the luminous property of the obtained light-emitting electrochemical cell 10 is shown in Table 5.

TABLE 4

| | Luminous Property | | | Organic | | Ionic Compound | |
| | Emission Luminance (cd/m2) | Voltage (V) | Additive | Polymeric Light-Emitting Material | Emission Color | Cation | Anion |
|---|---|---|---|---|---|---|---|
| Example 4-1 | 9,720 | 0.5 | TMP[7] | Super Yellow[2] | yellow | $N(C_4H_9\text{-n})_3(CH_3)^+$ | $PO_2(OC_4H_9\text{-n})_2^-$ |
| Example 4-2 | 13,766 | 0.5 | TEHP[11] | | | | |
| Example 4-3 | 9,220 | 0.5 | DINP[12] | | | | |
| Example 4-4 | 13,043 | 0.5 | DEHP[13] | | | | |
| Comparative Example 4 | 7,864 | 0.6 | none | | | | |

[2] Super Yellow: (phenylene-substituted poly(para-phenylene vinylene), manufactured by Merck KGaA, product name: PDY-132)
[7] TMP: trimethyl phosphate (manufacured by Kanto Chemical Co., Ltd.)
[11] TEHP: tris(2-ethylhexyl) phosphate (manufactured by Wako Pure Chemical Industries, Ltd.)
[12] DINP: diisononyl phthalate (manufactured by Kanto Chemical Co., Ltd.)
[13] DEHP: bis(2-ethylhexyl) phthalate (manufactured by Wako Pure Chemical Industries, Ltd.)

TABLE 5

| | Luminous Property | | | Organic | | Ionic Compound | |
|---|---|---|---|---|---|---|---|
| | Emission Luminance (cd/m$^2$) | Voltage (V) | Additive | Polymeric Light-Emitting Material | Emission Color | Cation | Anion |
| Example 5-1 | 423 | 9.0 | TMP[7] | PFO-spiro[1] | blue | $(C_4H_9\text{-}n)NC_3H_3N(CH_3)^+$ | $PO_2(OC_4H_9\text{-}n)_2^-$ |
| Example 5-2 | 822 | 8.5 | TEP[8] | | | | |
| Example 5-3 | 1,347 | 7.0 | TBP[3] | | | | |
| Example 5-4 | 1,025 | 5.5 | THP[9] | | | | |
| Example 5-5 | 622 | 6.7 | TEHP[11] | | | | |
| Example 5-6 | 469 | 11.0 | DBP[10] | | | | |
| Example 5-7 | 274 | 8.0 | DEHP[13] | | | | |
| Comparative Example 5 | 238 | 10.0 | none | | | | |

[1]PFO-spiro: (poly[(9,9-dioctylfluorenyl-2,7-diyl)-alt-co-(9,9'-spirobifluorene-2,7-diyl)], manufactured by Solaris Chem Inc., model number: SOL2412)
[3]TBP: tributyl phosphate (manufactured by Kanto Chemical Co., Ltd.)
[7]TMP: trimethyl phosphate (manufactured by Kanto Chemical Co., Ltd.)
[8]TEP: triethyl phosphate (manufactured by Kanto Chemical Co., Ltd.)
[9]THP: trihexyl phosphate (manufactured by Kanto Chemical Co., Ltd.)
[10]DBP: dibutyl phosphate (manufactured by Kanto Chemical Co., Ltd.)
[11]TEHP: tris(2-ethylhexyl) phosphate (manufactured by Wako Pure Chemical Industries, Ltd.)
[13]DEHP: bis(2-ethylhexyl) phthalate (manufactured by Wako Pure Chemical Industries, Ltd.)

Example 6-1 to 6-8

A commercially available glass substrate with an ITO film (manufactured by Geomatec Co., Ltd., ITO film thickness: 200 nm) was used as a first electrode 13.

There were used Super Yellow (phenylene-substituted poly(para-phenylene vinylene), manufactured by Merck KGaA, product name: PDY-132) as an organic polymeric light-emitting material, an imidazolium phosphate salt indicated in Table 6 as an ionic compound, and an additive being a compound indicated in Table 6; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material:the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 6.

Comparative Example 6

A light-emitting electrochemical cell 10 was fabricated by the same method as in Example 6-1 to 6-8, except for using no additive. The result of a measurement of the luminous property of the obtained light-emitting electrochemical cell 10 is shown in Table 6.

TABLE 6

| | Luminous Property | | | Organic | | Ionic Compound | |
|---|---|---|---|---|---|---|---|
| | Emission Luminance (cd/m$^2$) | Voltage (V) | Additive | Polymeric Light-Emitting Material | Emission Color | Cation | Anion |
| Example 6-1 | 449 | 13.0 | TMP[7] | Super Yellow[2] | yellow | $(C_4H_9\text{-}n)NC_3H_3N(CH_3)^+$ | $PO_2(OC_4H_9\text{-}n)_2^-$ |
| Example 6-2 | 1,524 | 11.5 | TEP[8] | | | | |
| Example 6-3 | 2,052 | 9.3 | TBP[3] | | | | |
| Example 6-4 | 1,796 | 7.0 | THP[9] | | | | |
| Example 6-5 | 171 | 5.0 | TEHP[11] | | | | |
| Example 6-6 | 1,896 | 5.0 | DBP[10] | | | | |
| Example 6-7 | 270 | 10.0 | DINP[12] | | | | |
| Example 6-8 | 98 | 11.0 | DEHP[13] | | | | |

TABLE 6-continued

| | Luminous Property | | | Organic | | Ionic Compound | |
|---|---|---|---|---|---|---|---|
| | Emission Luminance | Voltage | | Polymeric Light-Emitting | Emission | | |
| | (cd/m$^2$) | (V) | Additive | Material | Color | Cation | Anion |
| Comparative Example 6 | 29 | 11.0 | none | | | | |

[2]Super Yellow: (phenylene-substituted poly(para-phenylene vinylene), manufactured by Merck KGaA, product name: PDY-132)
[3]TBP: tributyl phosphate (manufactured by Kanto Chemical Co., Ltd.)
[7]TMP: trimethyl phosphate (manufactured by Kanto Chemical Co., Ltd.)
[8]TEP: triethyl phosphate (manufactured by Kanto Chemical Co., Ltd.)
[9]THP: trihexyl phosphate (manufactured by Kanto Chemical Co., Ltd.)
[10]DBP: dibutyl phosphate (manufactured by Kanto Chemical Co., Ltd.)
[11]TEHP: tris(2-ethylhexyl) phosphate (manufactured by Wako Pure Chemical Industries, Ltd.)
[12]DINP: diisononyl phthalate (manufactured by Kanto Chemical Co., Ltd.)
[13]DEHP: bis(2-ethylhexyl) phthalate (manufactured by Wako Pure Chemical Industries, Ltd.)

Example 7-1 to 7-2

A commercially available glass substrate with an ITO film (manufactured by Geomatec Co., Ltd., ITO film thickness: 200 nm) was used as a first electrode 13.

There were used PFO-spiro (poly[(9,9-dioctylfluorenyl-2,7-diyl)-alt-co-(9,9'-spirobifluorene-2,7-diyl)], manufactured by Solaris Chem Inc., model number: SOL2412) as an organic polymeric light-emitting material, a phosphonium (p-toluenesulfonyl) salt indicated in Table 7 as an ionic compound, and an additive being a compound indicated in Table 7; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material: the solution of the ionic compound: the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 7.

Comparative Example 7

A light-emitting electrochemical cell 10 was fabricated by the same method as in Example 7-1 to 7-2, except for using no additive. The result of a measurement of the luminous property of the obtained light-emitting electrochemical cell 10 is shown in Table 7.

TABLE 7

| | Luminous Property | | | Organic | | Ionic Compound | |
|---|---|---|---|---|---|---|---|
| | Emission Luminance | Voltage | | Polymeric Light-Emitting | Emission | | |
| | (cd/m$^2$) | (V) | Additive | Material | Color | Cation | Anion |
| Example 7-1 | 6,384 | 8.5 | TEHP[11] | PFO-spiro[1] | blue | P(C$_4$H$_9$-n)$_3$(C$_2$H$_5$)$^+$ | CH$_3$(C$_6$H$_4$)SO$_2^-$ |
| Example 7-2 | 10,033 | 8.6 | DEHP[13] | | | | |
| Comparative Example 7 | 272 | 11.0 | none | | | | |

[1]PFO-spiro: (poly[(9,9-dioctylfluorenyl-2,7-diyl)-alt-co-(9,9'-spirobifluorene-2,7-diyl)], manufactured by Solaris Chem Inc., model number: SOL2412)
[11]TEHP: tris(2-ethylhexyl) phosphate (manufactured by Wako Pure Chemical Industries, Ltd.)
[13]DEHP: bis(2-ethylhexyl) phthalate (manufactured by Wako Pure Chemical Industries, Ltd.)

Example 8-1 to 8-2

A commercially available glass substrate with an ITO film (manufactured by Geomatec Co., Ltd., ITO film thickness: 200 nm) was used as a first electrode 13.

There were used Super Yellow (phenylene-substituted poly(para-phenylene vinylene), manufactured by Merck KGaA, product name: PDY-132) as an organic polymeric light-emitting material, a phosphonium (p-toluenesulfonyl) salt indicated in Table 8 as an ionic compound, and an additive being a compound indicated in Table 8; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material: the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 8.

Comparative Example 8

A light-emitting electrochemical cell 10 was fabricated by the same method as in Example 8-1 to 8-2, except for using no additive. The result of a measurement of the luminous property of the obtained light-emitting electrochemical cell 10 is shown in Table 8.

compound, and an additive being a compound indicated in Table 9; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material: the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The

TABLE 8

| | Luminous Property | | | Organic Polymeric Light-Emitting Material | Emission Color | Ionic Compound | |
|---|---|---|---|---|---|---|---|
| | Emission Luminance (cd/m$^2$) | Voltage (V) | Additive | | | Cation | Anion |
| Example 8-1 | 2,171 | 5.5 | TEHP[11] | Super Yellow[2] | yellow | P(C$_4$H$_9$-n)$_3$(C$_2$H$_5$)$^+$ | CH$_3$(C$_6$F$_4$)SO$_2^-$ |
| Example 8-2 | 5,103 | 4.6 | DEHP[13] | | | | |
| Comparative Example 8 | 79 | 13.5 | none | | | | |

[2] Super Yellow: (phenylene-substituted poly(para-phenylene vinylene), manufactured by Merck KGaA, product name: PDY-132)
[11] TEHP: tris(2-ethylhexyl) phosphate (manufactured by Wako Pure Chemical Industries, Ltd.)
[13] DEHP: bis(2-ethylhexyl) phthalate (manufactured by Wako Pure Chemical Industries, Ltd.)

Example 9

A commercially available glass substrate with an ITO film (manufactured by Geomatec Co., Ltd., ITO film thickness: 200 nm) was used as a first electrode 13.

There were used PFO-spiro (poly[(9,9-dioctylfluorenyl-2,7-diyl)-alt-co-(9,9'-spirobifluorene-2,7-diyl)], manufactured by Solaris Chem Inc., model number: SOL2412) as an organic polymeric light-emitting material, a phosphonium (bis(oxalato)borate) salt indicated in Table 9 as an ionic result of a measurement of the luminous property of the obtained light-emitting electrochemical cell 10 is shown in Table 9.

Comparative Example 9

A light-emitting electrochemical cell 10 was fabricated by the same method as in Example 9, except for using no additive. The result of a measurement of the luminous property of the obtained light-emitting electrochemical cell 10 is shown in Table 9.

TABLE 9

| | Luminous Property | | | Organic Polymeric Light-Emitting Material | Emission Color | Ionic Compound | |
|---|---|---|---|---|---|---|---|
| | Emission Luminance (cd/m$^2$) | Voltage (V) | Additive | | | Cation | Anion |
| Example 9 | 3,293 | 7.7 | TEHP[11] | PFO-spiro[1] | blue | P(C$_8$H$_{17}$-n)$_3$(C$_{16}$H$_{33}$)$^+$ | B(C$_2$O$_4$)$_2^-$ |
| Comparative Example 9 | 365 | 12.0 | none | | | | |

[1] PFO-spiro: (poly[(9,9-dioctylfluorenyl-2,7-diyl)-alt-co-(9,9'-spirobifluorene-2,7-diyl)], manufactured by Solaris Chem Inc., model number: SOL2412)
[11] TEHP: tris(2-ethylhexyl) phosphate (manufactured by Wako Pure Chemical Industries, Ltd.)

Example 10

A commercially available glass substrate with an ITO film (manufactured by Geomatec Co., Ltd., ITO film thickness: 200 nm) was used as a first electrode 13.

There were used Super Yellow (phenylene-substituted poly(para-phenylene vinylene), manufactured by Merck KGaA, product name: PDY-132) as an organic polymeric light-emitting material, a phosphonium (bis(oxalato)borate) salt indicated in Table 10 as an ionic compound, and an additive being a compound indicated in Table 10; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material:the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 10.

Comparative Example 10

A light-emitting electrochemical cell 10 was fabricated by the same method as in Example 10, except for using no additive. The result of a measurement of the luminous property of the obtained light-emitting electrochemical cell 10 is shown in Table 10.

Example 11

A commercially available glass substrate with an ITO film (manufactured by Geomatec Co., Ltd., ITO film thickness: 200 nm) was used as a first electrode 13.

There were used PFO-spiro (poly[(9,9-dioctylfluorenyl-2,7-diyl)-alt-co-(9,9'-spirobifluorene-2,7-diyl)], manufactured by Solaris Chem Inc., model number: SOL2412) as an organic polymeric light-emitting material, a phosphonium (bistrifluoromethylsulfonylimide) salt indicated in Table 11 as an ionic compound, and an additive being a compound indicated in Table 11; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material:the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 11.

Comparative Example 11

A light-emitting electrochemical cell 10 was fabricated by the same method as in Example 11, except for using no additive. The result of a measurement of the luminous property of the obtained light-emitting electrochemical cell 10 is shown in Table 11.

TABLE 10

| | Luminous Property | | | Organic | | | |
| | Emission Luminance | Voltage | Additive | Polymeric Light-Emitting Material | Emission Color | Ionic Compound | |
| | (cd/m$^2$) | (V) | | | | Cation | Anion |
| Example 10 | 2,196 | 3.7 | DEHP[13] | Super Yellow[2] | yellow | P(C$_8$H$_{17}$-n)$_3$(C$_{16}$H$_{33}$)$^+$ | B(C$_2$O$_4$)$_2$$^-$ |
| Comparative Example 10 | 549 | 6.0 | none | | | | |

[2] Super Yellow: (phenylene-substituted poly(para-phenylene vinylene), manufactured by Merck KGaA, product name: PDY-132)
[13] DEHP: bis(2-ethylhexyl) phthalate (manufactured by Wako Pure Chemical Industries, Ltd.)

TABLE 11

| | Luminous Property | | | Organic | | Ionic Compound | |
|---|---|---|---|---|---|---|---|
| | Emission Luminance | Voltage | Additive | Polymeric Light-Emitting Material | Emission Color | Cation | Anion |
| | (cd/m$^2$) | (V) | | | | | |
| Example 11 | 92 | 12.0 | TEHP[11] | PFO-spiro[1] | blue | P(C$_4$H$_9$-n)$_3$(C$_8$H$_{17}$)$^+$ | N(CF$_3$SO$_2$)$_2^-$ |
| Comparative Example 11 | 47 | 12.0 | none | | | | |

[1]PFO-spiro: (poly[(9,9-dioctylfluorenyl-2,7-diyl)-alt-co-(9,9'-spirobifluorene-2,7-diyl)], manufactured by Solaris Chem Inc., model number: SOL2412)
[11]TEHP: tris(2-ethylhexyl) phosphate (manufactured by Wako Pure Chemical Industries, Ltd.)

Example 12-1 to 12-2

A commercially available glass substrate with an ITO film (manufactured by Geomatec Co., Ltd., ITO film thickness: 200 nm) was used as a first electrode 13.

There were used Super Yellow (phenylene-substituted poly(para-phenylene vinylene), manufactured by Merck KGaA, product name: PDY-132) as an organic polymeric light-emitting material, a phosphonium (bistrifluoromethylsulfonylimide) salt indicated in Table 12 as an ionic compound, and an additive being a compound indicated in Table 12; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material: the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 12.

Comparative Example 12

A light-emitting electrochemical cell 10 was fabricated by the same method as in Example 12-1 to 12-2, except for using no additive. The result of a measurement of the luminous property of the obtained light-emitting electrochemical cell 10 is shown in Table 12.

TABLE 12

| | Luminous Property | | | Organic | | Ionic Compound | |
|---|---|---|---|---|---|---|---|
| | Emission Luminance | Voltage | Additive | Polymeric Light-Emitting Material | Emission Color | Cation | Anion |
| | (cd/m$^2$) | (V) | | | | | |
| Example 12-1 | 2,124 | 2.9 | TEHP[11] | Super Yellow[2] | yellow | P(C$_4$H$_9$-n)$_3$(C$_8$H$_{17}$)$^+$ | N(CF$_3$SO$_2$)$_2^-$ |
| Example 12-2 | 1,432 | 3.2 | DEHP[13] | | | | |
| Comparative Example 12 | 97 | 13.0 | none | | | | |

[2]Super Yellow: (phenylene-substituted poly(para phenylene vinylene), manufactured by Merck KGaA, product name: PDY-132)
[11]TEHP: tris(2-ethylhexyl) phosphate (manufactured by Wako Pure Chemical Industries, Ltd.)
[13]DEHP: bis(2-ethylhexyl) phthalate (manufactured by Wako Pure Chemical Industries, Ltd.)

Example 13-1 to 13-2

A commercially available glass substrate with an ITO film (manufactured by Geomatec Co., Ltd., ITO film thickness: 200 nm) was used as a first electrode 13.

There were used PFO-spiro (poly[(9,9-dioctylfluorenyl-2,7-diyl)-alt-co-(9,9'-spirobifluorene-2,7-diyl)], manufactured by Solaris Chem Inc., model number: SOL2412) as an organic polymeric light-emitting material, a phosphonium (tetrafluoroborate) salt indicated in Table 13 as an ionic compound, and an additive being a compound indicated in Table 13; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material: the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 13.

Comparative Example 13

A light-emitting electrochemical cell 10 was fabricated by the same method as in Example 13-1 to 13-2, except for using no additive. The result of a measurement of the luminous property of the obtained light-emitting electrochemical cell 10 is shown in Table 13.

TABLE 13

| | Luminous Property | | | Organic | | | |
| | Emission Luminance | Voltage | Additive | Polymeric Light-Emitting Material | Emission Color | Ionic Compound | |
| | $(cd/m^2)$ | (V) | | | | Cation | Anion |
| Example 13-1 | 1.054 | 7.5 | TEHP[11] | PFO-spiro[1] | blue | $P(C_4H_9\text{-n})_3(C_8H_{17})^+$ | $BF_4^-$ |
| Example 13-2 | 431 | 9.7 | DEHP[13] | | | | |
| Comparative Example 13 | 85 | 12.0 | none | | | | |

[1]PFO-spiro: (poly[(9,9-dioctylfluorenyl-2,7-diyl)-alt-co-(9,9'-spirobifluorene-2,7-diyl)], manufactured by Solaris Chem Inc., model number: SOL2412)
[11]TEHP: tris(2-ethylhexyl) phosphate (manufactured by Wako Pure Chemical Industries, Ltd.)
[13]DEHP: bis(2-ethylhexyl) phthalate (manufactured by Wako Pure Chemical Industries, Ltd.)

Example 14-1 to 14-2

A commercially available glass substrate with an ITO film (manufactured by Geomatec Co., Ltd., ITO film thickness: 200 nm) was used as a first electrode 13.

There were used Super Yellow (phenylene-substituted poly(para-phenylene vinylene), manufactured by Merck KGaA, product name: PDY-132) as an organic polymeric light-emitting material, a phosphonium (tetrafluoroborate) salt indicated in Table 14 as an ionic compound, and an additive being a compound indicated in Table 14; and a mixed solution of these was prepared. Specifically, in a glove box in an argon atmosphere at room temperature, a toluene solution (concentration: 9 g/L) of the organic polymeric light-emitting material, a toluene solution (concentration: 9 g/L) of the ionic compound, and a toluene solution (concentration: 9 g/L) of the additive were mixed in the solution of the organic polymeric light-emitting material:the solution of the ionic compound; the solution of the additive=8:1:1 in volume ratio to thereby prepare a composition for forming a light-emitting layer.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 50° C. for 30 min to thereby evaporate the organic solvent. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. A light-emitting electrochemical cell 10 having an area of 2 mm×2 mm square to become a predetermined light-emitting portion was thus fabricated. The result of a measurement of the luminous property of the obtained light-emitting electrochemical cell 10 is shown in Table 14.

Comparative Example 14

A light-emitting electrochemical cell 10 was fabricated by the same method as in Example 14-1 to 14-2, except for using no additive. The result of a measurement of the luminous property of the obtained light-emitting electrochemical cell 10 is shown in Table 14.

TABLE 14

| | Luminous Property | | | Organic Polymeric Light-Emitting Material | Emission Color | Ionic Compound | |
|---|---|---|---|---|---|---|---|
| | Emission Luminance | Voltage | | | | | |
| | (cd/m$^2$) | (V) | Additive | | | Cation | Anion |
| Example 14-1 | 1,548 | 3.1 | TEHP[11] | Super Yellow[2] | yellow | P(C$_4$H$_9$-n)$_3$(C$_8$H$_{17}$)$^+$ | BF$_4^-$ |
| Example 14-2 | 611 | 3.4 | DEHP[13] | | | | |
| Comparative Example 14 | 409 | 13.5 | none | | | | |

[2] Super Yellow: (phenylene-substituted poly(para-phenylene vinylene), manufactured by Merck KGaA, product name: PDY-132)
[11] TEHP: tris(2-ethylhexyl) phosphate (manufactured by Wako Pure Chemical Industries, Ltd.)
[13] DEHP: bis(2-ethylhexyl) phthalate (manufactured by Wako Pure Chemical Industries, Ltd.)

As is clear from the results indicated in Table 1 to Table 14, it was proved that the light-emitting electrochemical cell of each Example, in which a compound represented by the general formula (1) was added to its light-emitting layer, was improved in the compatibility of an ionic compound with a light-emitting material, resultantly exhibited a higher emission luminance than the light-emitting electrochemical cell of each Comparative Example, in which no additive represented by the general formula (1) was added or a compound other than the general formula (1) was added, and with a lower voltage at this time, could be driven at a lower voltage.

Examples 15-1 to 15-6

Commercially available glass substrates with an ITO film (manufactured by Geomatec Co., Ltd., ITO film thickness: 200 nm) were used as first electrodes 13.

There were used Super Yellow (phenylene-substituted poly(para-phenylene vinylene), manufactured by Merck KGaA, product name: PDY-132) as an organic polymeric light-emitting material, ionic compounds (metal salts) indicated in Table 15 and additives being compounds indicated in Table 15; and mixed solutions of these were prepared, respectively. Specifically, in a glove box in an argon atmosphere at room temperature, a cyclohexanone solution (concentration: 9 g/L) of the organic polymeric light-emitting material, a cyclohexanone solution (concentration: 9 g/L) of the metal salt, and a cyclohexanone solution (concentration: 9 g/L) of the additive were mixed in the solution of the organic polymeric light-emitting material:the solution of the metal salt; the solution of the additive=80:5:10 in volume ratio to thereby prepare compositions for forming light-emitting layers.

Then, in a glove box in an argon atmosphere at room temperature, the prepared composition for forming a light-emitting layer was applied by spin coating on the first electrode 13 of the glass substrate to thereby make a film; and the resultant was heated on a hot plate at 80° C. for 60 min to thereby evaporate the cyclohexanone. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. Light-emitting electrochemical cells 10 having an area of 2 mm×2 mm square to each become a predetermined light-emitting portion were thus fabricated. The result of measurements of the luminous property of the obtained light-emitting electrochemical cells 10 are shown in Table 15.

Comparative Example 15

A light-emitting electrochemical cell 10 was fabricated by the same method as in Example 15-1 to 15-6, except for using no additive. The result of a measurement of the luminous property of the obtained light-emitting electrochemical cell 10 is shown in Table 15.

TABLE 15

| | Luminous Property | | | Organic Polymeric Light-Emitting Material | Emission Color | Ionic Compound (metal salt) | |
|---|---|---|---|---|---|---|---|
| | Emission Luminance | Voltage | | | | | |
| | (cd/m$^2$) | (V) | Additive | | | Cation | Anion |
| Example 15-1 | 2,200 | 8.7 | TBP[3] | Super Yellow[2] | yellow | Li$^+$ | N(CF$_3$SO$_2$)$_2^-$ |
| Example 15-2 | 1,600 | 9.2 | DBP[14] | | | | |
| Example 15-3 | 1,000 | 9.6 | BuBz[15] | | | | |
| Example 15-4 | 820 | 10.6 | BuTs[16] | | | | |
| Example 15-5 | 1,100 | 10.1 | PC[17] | | | | |
| Example 15-6 | 980 | 10.2 | DEC[18] | | | | |

TABLE 15-continued

| | Luminous Property | | | Organic | | Ionic Compound (metal salt) | |
|---|---|---|---|---|---|---|---|
| | Emission Luminance | Voltage | | Polymeric Light-Emitting | Emission | | |
| | (cd/m²) | (V) | Additive | Material | Color | Cation | Anion |
| Comparative Example 15 | 0 | — | none | | | | |

[2]Super Yellow: (phenylene-substituted poly(para-phenylene vinylene), manufactured by Merck KGaA, product name: PDY-132)
[3]TBP: tributyl phosphate (manufactured by Kanto Chemical Co., Ltd.)
[14]DBP: dibutyl phthalate (manufactured by Tokyo Chemical Industry Co., Ltd.)
[15]BuBz: butyl benzoate (manufactured by Tokyo Chemical Industry Co., Ltd.)
[16]BuTs: butyl p-toluenesulfonate (manufactured by Tokyo Chemical Industry Co., Ltd.)
[17]PC: propylene carbonate (manufactured by Kanto Chemical Co., Ltd.)
[18]DEC: diethyl carbonate (manufactured by Kanto Chemical Co., Ltd.)

Examples 16

Commercially available glass substrates with an ITO film (manufactured by Geomatec Co., Ltd., ITO film thickness: 200 nm) were used as first electrodes 13.

There were used Super Yellow (phenylene-substituted poly(para-phenylene vinylene), manufactured by Merck KGaA, product name: PDY-132) as an organic polymeric light-emitting material, ionic compounds (metal salts) indicated in Table 16 and additives being compounds indicated in Table 16; and mixed solutions of these were prepared, respectively. Specifically, in a glove box in an argon atmosphere at room temperature, a cyclohexanone solution (concentration: 9 g/L) of the organic polymeric light-emitting material, a cyclohexanone solution (concentration: 9 g/L) of the metal salt, and a cyclohexanone solution (concentration: 9 g/L) of the additive were mixed in the solution of the organic polymeric light-emitting material:the solution of the metal salt; the solution of the additive=80:5:10 in volume ratio to thereby prepare compositions for forming light-emitting layers.

Then, for the each composition, in a glove box in an argon atmosphere at room temperature, the prepared composition for forming a light-emitting layer was applied by spin coating on the first electrode 13 of the glass substrate to thereby make a film; and the resultant was heated on a hot plate at 80° C. for 60 min to thereby evaporate the cyclohexanone. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. Light-emitting electrochemical cells 10 having an area of 2 mm×2 mm square to each become a predetermined light-emitting portion were thus fabricated. The result of measurements of the luminous property of the obtained light-emitting electrochemical cells 10 are shown in Table 15.

Comparative Example 16

A light-emitting electrochemical cell 10 was fabricated by the same method as in Example 16, except for using no additive. The result of a measurement of the luminous property of the obtained light-emitting electrochemical cell 10 is shown in Table 16.

TABLE 16

| | Luminous Property | | | Organic | | Ionic Compound (metal salt) | |
|---|---|---|---|---|---|---|---|
| | Emission Luminance | Voltage | | Polymeric Light-Emitting | Emission | | |
| | (cd/m²) | (V) | Additive | Material | Color | Cation | Anion |
| Example 16 | 1,600 | 8.8 | TBP[3] | Super Yellow[2] | yellow | K⁺ | CF$_3$SO$_3^-$ |
| Comparative Example 16 | 0 | — | none | | | | |

[2]Super Yellow: (phenylene-substituted poly(para-phenylene vinylene), manufactured by Merck KGaA, product name: PDY-132)
[3]TBP: tributyl phosphate (manufactured by Kanto Chemical Co., Ltd.)

Examples 17-1 to 17-2

Commercially available glass substrates with an ITO film (manufactured by Geomatec Co., Ltd., ITO film thickness: 200 nm) were used as first electrodes 13.

There were used PFO-spiro (poly[(9,9-dioctylfluorenyl-2,7-diyl)-alt-co-(9,9,9'-spirobifluorene-2,7-diyl)], manufactured by Solaris Chem Inc., model number: SOL2412) as an organic polymeric light-emitting material, ionic compounds (metal salts) indicated in Table 17 and additives being compounds indicated in Table 17; and mixed solutions of these was prepared, respectively. Specifically, in a glove box in an argon atmosphere at room temperature, a cyclohexanone solution (concentration: 9 g/L) of the organic polymeric light-emitting material, a cyclohexanone solution (concentration: 9 g/L) of the metal salt, and a cyclohexanone solution (concentration: 9 g/L) of the additive were mixed in the solution of the organic polymeric light-emitting material: the solution of the metal salt; the solution of the additive=80:5:10 in volume ratio to thereby prepare compositions for forming light-emitting layers.

Then, for the each composition, in a glove box in an argon atmosphere at room temperature, the prepared composition for forming a light-emitting layer was applied by spin coating on the first electrode 13 of the glass substrate to thereby make a film; and the resultant was heated on a hot plate at 80° C. for 60 min to thereby evaporate the cyclohexanone. A solid-state light-emitting layer 12 having a film thickness of 100 nm was thus formed. Further on the formed light-emitting layer 12, a second electrode 14 composed of aluminum (Al) having a thickness of 50 nm was formed by the above-mentioned method. Light-emitting electrochemical cells 10 having an area of 2 mm×2 mm square to each become a predetermined light-emitting portion were thus fabricated. The result of measurements of the luminous property of the obtained light-emitting electrochemical cells 10 are shown in Table 15.

Comparative Example 17

A light-emitting electrochemical cell 10 was fabricated by the same method as in Example 17-1 to 17-2, except for using no additive. The result of a measurement of the luminous property of the obtained light-emitting electrochemical cell 10 is shown in Table 17.

TABLE 17

| | Luminous Property | | | Organic | | Ionic Compound (metal salt) | |
| | Emission Luminance | Voltage | | Polymeric Light-Emitting | Emission | | |
| | (cd/m$^2$) | (V) | Additive | Material | Color | Cation | Anion |
| Example 17-1 | 870 | 9.1 | TBP[3] | PFO-spiro[1] | blue | Li$^+$ | N(CF$_3$SO$_2$)$_2^-$ |
| Example 17-2 | 550 | 11.3 | DBP[14] | | | | |
| Comparative Example 17 | 0 | — | none | | | | |

[1] PFO-spiro: (poly[(9,9-dioctylfluorenyl-2,7-diyl)-alt-co-(9,9'spirobifluorene-2,7-diyl)], manufactured by Solaris Chem Inc., model number: SOL2412)
[3] TBP: tributyl phosphate (manufactured by Kanto Chemical Co., Ltd.)
[14] DBP: dibutyl phthalate (manufactured by Tokyo Chemical Industry Co., Ltd.)

REFERENCE SIGNS LIST

10 LIGHT-EMITTING ELECTROCHEMICAL CELL
12 LIGHT-EMITTING LAYER
13 FIRST ELECTRODE
14 SECOND ELECTRODE
16 p-DOPED REGION
17 n-DOPED REGION

The invention claimed is:

1. An additive for a light-emitting layer of a light-emitting electrochemical cell, comprising a compound represented by the following general formula (2) wherein the light-emitting electrochemical cell comprises a light-emitting layer comprising a light-emitting material and an ionic compound; and the compound represented by the general formula (2) is contained in an amount of 5% by mass or more and 20% by mass or less in the light-emitting layer:

(2)

wherein
R is a hydrogen atom or a branched-chain, straight-chain or cyclic alkyl group; each R may be identical or different; the plurality of R bonded to the same phosphorous atom through O may be linked mutually and form a ring; and when the ring is not formed, at least one R is an alkyl group;

wherein the ionic compound includes an anion selected from the group consisting of benzotriazolate (N$_3$(C$_6$H$_4$)), tetraphenylborate (B(C$_6$H$_5$)$_4$), bis(trifluoromethylsulfonyl)imide (N(CF$_3$SO$_2$)$_2$), trifluoromethanesulfonate (SO$_3$CF$_3$), methanesulfonate (SO$_3$CH$_3$), tris(pentafluoroethyl)trifluorophosphate ((C$_2$H$_5$)$_3$PF$_3$), trifluoroacetic acid (CF$_3$COO), amino acids, bisoxalatoborate (B(C$_2$O$_4$)$_2$), p-toluenesulfonate (CH$_3$C$_6$H$_4$SO$_3$), p-toluenesulfonyl (CH$_3$C$_6$H$_4$SO$_2$), mesitylenesulfonyl ((CH$_3$)$_3$C$_6$H$_4$SO$_2$), dimethylbenzenesulfonyl ((CH$_3$)$_2$C$_6$H$_4$SO$_2$), thiocyanate (SCN), dicyanamide (N(CN)$_2$), a phosphate ester represented by the following general formula (7), a sulfate ester anion represented by the following general formula (8), dithiophosphorous acid represented by the following general formula (9) or an aliphatic carboxylic acid represented by the following general formula (10), $$PO_2(OR_7)_2 \tag{7}$$

wherein R$_7$ is an alkyl group having 1 or more and 20 or less carbon atoms, and two R$_7$ may be the same or different, $$SO_3(OR_8) \tag{8}$$

wherein R$_8$ is an alkyl group having 1 or more and 20 or less carbon atoms, $$(R_9O)_2PSS \tag{9}$$

wherein R$_9$ is an alkyl group having 1 or more and 20 or less carbon atoms, and two R$_9$ may be the same or different, $$R_{10}CO_2 \tag{10}$$

wherein R$_{10}$ is an alkyl group having 1 or more and 20 or less carbon atoms.

2. An additive for a light-emitting electrochemical cell, comprising a compound represented by the following general formula (3) wherein the light-emitting electrochemical cell comprises a light-emitting layer comprising a light-emitting material and an ionic compound; and the compound represented by the general formula (3) is contained in an amount of 5% by mass or more and 20% by mass or less in the light-emitting layer:

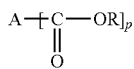

(3)

wherein A is an aromatic hydrocarbon group, an alicyclic hydrocarbon group or a heterocyclic group;

R is a hydrogen atom or a branched-chain, straight-chain or cyclic alkyl group; when a plurality of R are present, they may be identical or different the plurality of R bonded to the same carbon atom through O may be linked mutually and form a ring; and when the ring is not formed, at least one R is an alkyl group; and p is a substitutable number on A.

3. An additive for a light-emitting layer of a light-emitting electrochemical cell, comprising a compound represented by the following general formula (a) wherein the light-emitting electrochemical cell comprises a light-emitting layer comprising a light-emitting material and an ionic compound; and the compound represented by the general formula (a) is contained in an amount of 5% by mass or more and 20% by mass or less in the light-emitting layer:

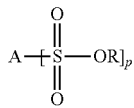

(a)

wherein A is an aromatic hydrocarbon group, a chain aliphatic hydrocarbon group, an alicyclic hydrocarbon group or a heterocyclic group, R is a hydrogen atom or a branched-chain, straight-chain or cyclic alkyl group; when a plurality of R are present, they may be identical or different the plurality of R bonded to the same sulfur atom through O may be linked mutually and form a ring; and when the ring is not formed, at least one R is an alkyl group; and p is a substitutable number on A.

4. The additive according to claim 1, wherein the additive is used for improving dispersibility of the ionic compound in the light-emitting material.

5. A composition for forming a light-emitting layer of a light-emitting electrochemical cell, comprising a compound represented by the following general formula (2), an ionic compound and a light-emitting material:

(2)

wherein R is a hydrogen atom or a branched-chain, straight-chain or cyclic alkyl group; each R may be identical or different; the plurality of R bonded to the same phosphorous atom through O may be linked mutually and form a ring; and at least one R is an alkyl group wherein the ionic compound is represented by the following general formula (4) or the following general formula (5), in the formula (4), one or more groups out of $R_1$, $R_2$, $R_3$ and $R_4$ are alkyl groups having a difference in the number of carbon atoms of 5 or smaller from the alkyl groups represented by R of the compound represented by the general formula (2), and in the formula (5), $R_6$ is an alkyl group having a difference in the number of carbon atoms of 5 or smaller from the alkyl groups represented by R of the compound represented by the general formula (2),

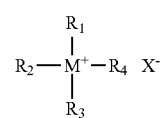

(4)

wherein $R_1$, $R_2$, $R_3$ and $R_4$ each denote an alkyl group, an alkoxyalkyl group, a trialkylsilylalkyl group, an alkenyl group, an alkynyl group, an aryl group or a heterocyclic group, which groups each may be substituted with a functional group; $R_1$, $R_2$, $R_3$ and $R_4$ may be the same or different from one another; M denotes N or P; and $X^-$ denotes an anion,

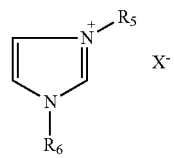

(5)

wherein $R_5$ denotes an alkyl group, an alkoxyalkyl group, a trialkylsilylalkyl group, an alkenyl group, an alkynyl group, an aryl group or a heterocyclic group, $R_6$ denotes an alkyl group, each which groups each may be substituted with a functional group; $R_5$ and $R_6$ may be the same or different from each other; and $X^-$ denotes an anion.

6. The composition for forming a light-emitting layer according to claim 5, wherein a cation of the ionic compound is at least one selected from a phosphonium cation, an ammonium cation and an imidazolium cation.

7. The composition for forming a light-emitting layer according to claim 5, wherein a cation of the ionic compound is a cation of at least one metal selected from Li, Na, K, Cs, Mg and Ca.

8. The composition for forming a light-emitting layer according to claim 5, wherein the composition contains the compound represented by the general formula (2) in an amount of 0.0001% by mass or larger and 10% by mass or smaller.

9. The composition for forming a light-emitting layer according to claim 5, wherein the light-emitting material is an organic polymeric light-emitting material of a polymer of paraphenylene vinylene, fluorene, 1,4-phenylene, thiophene, pyrrole, paraphenylene sulfide, benzothiazole, biothiophine or a derivative of these, or a copolymer containing these.

10. A light-emitting electrochemical cell, comprising a light-emitting layer and an electrode disposed on each surface thereof, wherein the light-emitting layer comprises a light-emitting material, an ionic compound and a compound represented by the following general formula (2):

 (2)

wherein R is a hydrogen atom or a branched-chain, straight-chain or cyclic alkyl group; each R may be identical or different; the plurality of R bonded to the same phosphorous atom through O may be linked mutually and form a ring; and at least one R is an alkyl group,
  wherein the ionic compound is represented by the following general formula (4) or the following general formula (5),
  in the formula (4), one or more groups out of $R_1$, $R_2$, $R_3$ and $R_4$ are alkyl groups having a difference in the number of carbon atoms of 5 or smaller from the alkyl groups represented by R of the compound represented by the general formula (2), and
  in the formula (5), $R_6$ is an alkyl group having a difference in the number of carbon atoms of 5 or smaller from the alkyl groups represented by R of the compound represented by the general formula (2),

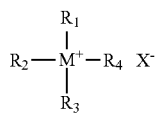 (4)

wherein $R_1$, $R_2$, $R_3$ and $R_4$ each denote an alkyl group, an alkoxyalkyl group, a trialkylsilylalkyl group, an alkenyl group, an alkynyl group, an aryl group or a heterocyclic group, which groups each may be substituted with a functional group; $R_1$, $R_2$, $R_3$ and $R_4$ may be the same or different from one another; M denotes N or P; and $X^-$ denotes an anion,

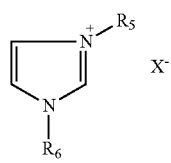 (5)

wherein $R_5$ denotes an alkyl group, an alkoxyalkyl group, a trialkylsilylalkyl group, an alkenyl group, an alkynyl group, an aryl group or a heterocyclic group, $R_6$ denotes an alkyl group, each which groups each may be substituted with a functional group; $R_5$ and $R_6$ may be the same or different from each other; and $X^-$ denotes an anion.

11. The light-emitting electrochemical cell according to claim 10, wherein a cation of the ionic compound is at least one selected from a phosphonium cation, an ammonium cation and an imidazolium cation.

12. The light-emitting electrochemical cell according to claim 10, wherein a cation of the ionic compound is a cation of at least one metal selected from Li, Na, K, Cs, Mg and Ca.

13. The light-emitting electrochemical cell according to claim 10, wherein the compound represented by the general formula (2) is contained in 1% by mass or more and 20% by mass or less in the light-emitting layer.

14. The light-emitting electrochemical cell according to claim 10, wherein the light-emitting material is an organic polymeric light-emitting material of a polymer of paraphenylene vinylene, fluorene, 1,4-phenylene, thiophene, pyrrole, paraphenylene sulfide, benzothiazole, biothiophine or a derivative of these, or a copolymer containing these.

15. An additive for a light-emitting layer of a light-emitting electrochemical cell, comprising a compound represented by the following general formula (3) or (a):

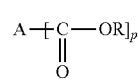 (3)

wherein A is an aromatic hydrocarbon group, an alicyclic hydrocarbon group or a heterocyclic group;
  R is a hydrogen atom or a branched-chain, straight-chain or cyclic alkyl group; when a plurality of R are present, they may be identical or different; the plurality of R bonded to the same carbon atom through O may be linked mutually and form a ring; and when the ring is not formed, at least one R is an alkyl group;
  p is 1 when A is a hydrogen atom, is 2 when A is a direct bond, and is a substitutable number on A when A is not a hydrogen atom or a direct bond,

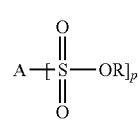 (a)

wherein A is an aromatic hydrocarbon group, a chain aliphatic hydrocarbon group, an alicyclic hydrocarbon group or a heterocyclic group;
  R is a hydrogen atom or a branched-chain, straight-chain or cyclic alkyl group; when a plurality of R are present, they may be identical or different; the plurality of R bonded to the same sulfur atom through O may be linked mutually and form a ring; and when the ring is not formed, at least one R is an alkyl group; and
  p is a substitutable number on A.

16. The additive according to claim 15, wherein the light-emitting electrochemical cell comprises a light-emitting layer comprising a light-emitting material and an ionic compound; and the additive is used for improving dispersibility of the ionic compound in the light-emitting material.

17. The additive according to claim 15, wherein the light-emitting electrochemical cell comprises a light-emitting layer comprising a light-emitting material and an ionic compound; and the compound represented by the general formula (3) or (a) is contained in an amount of 1% by mass or more and 20% by mass or less in the light-emitting layer.

18. A composition for forming a light-emitting layer of a light-emitting electrochemical cell, comprising a compound represented by the following general formula (3) or (a), an ionic compound and a light-emitting material:

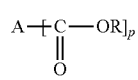 (3)

wherein A is an aromatic hydrocarbon group, an alicyclic hydrocarbon group or a heterocyclic group;
  R is a hydrogen atom or a branched-chain, straight-chain or cyclic alkyl group; when a plurality of R are present, they may be identical or different; the plurality of R bonded to the same carbon atom through O may be linked mutually and form a ring; and when the ring is not formed, at least one R is an alkyl group;

p is 1 when A is a hydrogen atom, is 2 when A is a direct bond, and is a substitutable number on A when A is not a hydrogen atom or a direct bond,

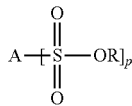

(a)

wherein A is an aromatic hydrocarbon group, a chain aliphatic hydrocarbon group, an alicyclic hydrocarbon group or a heterocyclic group;

R is a hydrogen atom or a branched-chain, straight-chain or cyclic alkyl group; when a plurality of R are present, they may be identical or different; the plurality of R bonded to the same sulfur atom through O may be linked mutually and form a ring; and when the ring is not formed, at least one R is an alkyl group; and p is a substitutable number on A.

19. The composition for forming a light-emitting layer according to claim 18, wherein a cation of the ionic compound is at least one selected from a phosphonium cation, an ammonium cation and an imidazolium cation.

20. The composition for forming a light-emitting layer according to claim 18, wherein a cation of the ionic compound is a cation of at least one metal selected from Li, Na, K, Cs, Mg and Ca.

21. The composition for forming a light-emitting layer according to claim 18, wherein the composition contains the compound represented by the general formula (3) or (a), in an amount of 0.0001% by mass or larger and 10% by mass or smaller.

22. The composition for forming a light-emitting layer according to claim 18, wherein the light-emitting material is an organic polymeric light-emitting material of a polymer of paraphenylene vinylene, fluorene, 1,4-phenylene, thiophene, pyrrole, paraphenylene sulfide, benzothiazole, biothiophine or a derivative of these, or a copolymer containing these.

23. A light-emitting electrochemical cell, comprising a light-emitting layer and an electrode disposed on each surface thereof, wherein the light-emitting layer comprises a light-emitting material, an ionic compound and a compound represented by the following general formula (3) or (a):

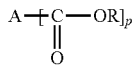

(3)

wherein A is an aromatic hydrocarbon group, an alicyclic hydrocarbon group or a heterocyclic group;

R is a hydrogen atom or a branched-chain, straight-chain or cyclic alkyl group; when a plurality of R are present, they may be identical or different; the plurality of R bonded to the same carbon atom through O may be linked mutually and form a ring; and when the ring is not formed, at least one R is an alkyl group;

p is 1 when A is a hydrogen atom, is 2 when A is a direct bond, and is a substitutable number on A when A is not a hydrogen atom or a direct bond,

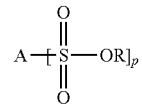

(a)

wherein A is an aromatic hydrocarbon group, a chain aliphatic hydrocarbon group, an alicyclic hydrocarbon group or a heterocyclic group;

R is a hydrogen atom or a branched-chain, straight-chain or cyclic alkyl group; when a plurality of R are present, they may be identical or different; the plurality of R bonded to the same sulfur atom through O may be linked mutually and form a ring; and when the ring is not formed, at least one R is an alkyl group; and p is a substitutable number on A.

24. The light-emitting electrochemical cell according to claim 23, wherein a cation of the ionic compound is at least one selected from a phosphonium cation, an ammonium cation and an imidazolium cation.

25. The light-emitting electrochemical cell according to claim 23, wherein a cation of the ionic compound is a cation of at least one metal selected from Li, Na, K, Cs, Mg and Ca.

26. The light-emitting electrochemical cell according to claim 23, wherein the compound represented by the general formula (3) or (a) is contained in 1% by mass or more and 20% by mass or less in the light-emitting layer.

27. The light-emitting electrochemical cell according to claim 23, wherein the light-emitting material is an organic polymeric light-emitting material of a polymer of paraphenylene vinylene, fluorene, 1,4-phenylene, thiophene, pyrrole, paraphenylene sulfide, benzothiazole, biothiophine or a derivative of these, or a copolymer containing these.

28. A composition for forming a light-emitting layer according to claim 5, wherein the content of the compound represented by the general formula (2) in the light-emitting layer is 2 parts by mass or higher and 30 parts by mass or lower to 100 parts by mass of the light-emitting material.

29. A composition for forming a light-emitting layer of a light-emitting electrochemical cell, comprising a compound represented by the following general formula (2), an ionic compound and a light-emitting material:

(2)

wherein R is a hydrogen atom or a branched-chain, straight-chain or cyclic alkyl group; each R may be identical or different the plurality of R bonded to the same phosphorous atom through O may be linked mutually and form a ring; and when the ring is not formed, at least one R is an alkyl group;

wherein the anion of the ionic compound is selected from among benzotriazolate ($N_3(C_6H_4)$), tris(pentafluoroethyl)trifluorophosphate (($C_2H_5)_3PF_3$), amino acids, bisoxalatoborate ($B(C_2O_4)_2$), p-toluenesulfonyl ($CH_3C_6H_4SO_2$), mesitylenesulfonyl (($CH_3)_3C_6H_4SO_2$), dimethylbenzenesulfonyl (($CH_3)_2C_6H_4SO_2$), phosphate esters represented by the following general formula (7), dithiophosphorous acid represented by the following general formula (9) and aliphatic carboxylic acids represented by the following general formula (10), $$PO_2(OR_7)_2 \quad (7)$$

wherein $R_7$ is an alkyl group having 1 or more and 20 or less carbon atoms, and two $R_7$ may be the same or different, $$(R_9O)_2PSS \qquad (9)$$

wherein $R_9$ is an alkyl group having 1 or more and 20 or less carbon atoms, and two $R_9$ may be the same or different, $$R_{10}CO_2 \qquad (10)$$

wherein $R_{10}$ is an alkyl group having 1 or more and 20 or less carbon atoms.

30. The light-emitting electrochemical cell according to claim 10, wherein wherein the content of the compound represented by the general formula (2) in the light-emitting layer is 2 parts by mass or higher and 30 parts by mass or lower to 100 parts by mass of the light-emitting material.

31. A light-emitting electrochemical cell, comprising a light-emitting layer and an electrode disposed on each surface thereof,
wherein the light-emitting layer comprises a light-emitting material, an ionic compound and a compound represented by the following general formula (2):

(2)

wherein R is a hydrogen atom or a branched-chain, straight-chain or cyclic alkyl group; each R may be identical or different the plurality of R bonded to the same phosphorous atom through O may be linked mutually and form a ring; and when the ring is not formed, at least one R is an alkyl group,
wherein the anion of the ionic compound is selected from among benzotriazolate ($N_3(C_6H_4)$), tris(pentafluoroethyl)trifluorophosphate ($(C_2H_5)_3PF_3$), amino acids, bisoxalatoborate ($B(C_2O_4)_2$), p-toluenesulfonyl ($CH_3C_6H_4SO_2$), mesitylenesulfonyl ($(CH_3)_3C_6H_4SO_2$), dimethylbenzenesulfonyl ($(CH_3)_2C_6H_4SO_2$), phosphate esters represented by the following general formula (7), dithiophosphorous acid represented by the following general formula (9) and aliphatic carboxylic acids represented by the following general formula (10), $$PO_2(OR_7)_2 \qquad (7)$$

wherein $R_7$ is an alkyl group having 1 or more and 20 or less carbon atoms, and two $R_7$ may be the same or different, $$(R_9O)_2PSS \qquad (9)$$

wherein $R_9$ is an alkyl group having 1 or more and 20 or less carbon atoms, and two $R_9$ may be the same or different, $$R_{10}CO_2 \qquad (10)$$

wherein $R_{10}$ is an alkyl group having 1 or more and 20 or less carbon atoms.

32. A composition for forming a light-emitting layer of a light-emitting electrochemical cell, comprising a compound represented by the following general formula (2), an ionic compound and a light-emitting material:

(2)

wherein R is a hydrogen atom or a branched-chain, straight-chain or cyclic alkyl group; each R may be identical or different; the plurality of R bonded to the same phosphorous atom through O may be linked mutually and form a ring; and when the ring is not formed, at least one R is an alkyl group;
wherein the anion of the ionic compound is selected from among bis(fluorosulfonyl)imide ($N(SO_2F)_2$) and hypophosphorous acid.

33. A light-emitting electrochemical cell, comprising a light-emitting layer and an electrode disposed on each surface thereof,
wherein the light-emitting layer comprises a light-emitting material, an ionic compound and a compound represented by the following general formula (2):

(2)

wherein R is a hydrogen atom or a branched-chain, straight-chain or cyclic alkyl group; each R may be identical or different; the plurality of R bonded to the same phosphorous atom through O may be linked mutually and form a ring; and when the ring is not formed, at least one R is an alkyl group,
wherein the anion of the ionic compound is selected from among wherein the anion of the ionic compound is selected from among bis(fluorosulfonyl)imide ($N(SO_2F)_2$) and hypophosphorous acid.

34. An additive for a light-emitting layer of a light-emitting electrochemical cell, comprising a compound represented by the following general formula (2) wherein the light-emitting electrochemical cell comprises a light-emitting layer comprising a light-emitting material and an ionic compound; and the compound represented by the general formula (2) is contained in an amount of 5% by mass or more and 20% by mass or less in the light-emitting layer:

(2)

wherein R is a hydrogen atom or a branched-chain, straight-chain or cyclic alkyl group; each R may be identical or different; the plurality of R bonded to the same phosphorous atom through O may be linked mutually and form a ring; and when the ring is not formed, at least one R is an alkyl group;
wherein the ionic compound includes an anion selected from the group consisting of fluorine, bromine, iodine, chlorine, tetrafluoroborate ($BF_4$), hexafluorophosphate ($PF_6$), bis(fluorosulfonyl)imide ($N(SO_2F)_2$) and hypophosphorous acid.

* * * * *